US011819564B2

(12) United States Patent
Shiroya et al.

(10) Patent No.: US 11,819,564 B2
(45) Date of Patent: *Nov. 21, 2023

(54) COMPOSITION COMPRISING POLYION COMPLEX PARTICLE AND OIL

(71) Applicant: L'Oreal, Paris (FR)

(72) Inventors: Toshifumi Shiroya, Kawasaki (JP); Hidehiko Asanuma, Kawasaki (JP); Takehiko Kasai, Kawasaki (JP)

(73) Assignee: L'Oreal, Paris (FR)

( * ) Notice: Subject to any disclaimer, the term of this patent is extended or adjusted under 35 U.S.C. 154(b) by 45 days.

This patent is subject to a terminal disclaimer.

(21) Appl. No.: 16/619,887

(22) PCT Filed: Jun. 8, 2018

(86) PCT No.: PCT/JP2018/022819
§ 371 (c)(1),
(2) Date: Dec. 5, 2019

(87) PCT Pub. No.: WO2018/230673
PCT Pub. Date: Dec. 20, 2018

(65) Prior Publication Data
US 2020/0163866 A1 May 28, 2020

(30) Foreign Application Priority Data

Jun. 13, 2017 (JP) ................. 2017-115764

(51) Int. Cl.
| | |
|---|---|
| *A61K 8/92* | (2006.01) |
| *A61K 8/06* | (2006.01) |
| *A61K 8/73* | (2006.01) |
| *A61K 8/81* | (2006.01) |
| *A61K 8/88* | (2006.01) |
| *A61Q 19/00* | (2006.01) |

(52) U.S. Cl.
CPC ............... *A61K 8/92* (2013.01); *A61K 8/062* (2013.01); *A61K 8/731* (2013.01); *A61K 8/733* (2013.01); *A61K 8/735* (2013.01); *A61K 8/736* (2013.01); *A61K 8/8152* (2013.01); *A61K 8/8164* (2013.01); *A61K 8/88* (2013.01); *A61Q 19/007* (2013.01)

(58) Field of Classification Search
CPC .................................... A61Q 19/10
See application file for complete search history.

(56) References Cited

U.S. PATENT DOCUMENTS

| | | | |
|---|---|---|---|
| 3,590,118 A | 6/1971 | Conrady et al. | |
| 4,524,061 A | 6/1985 | Cho et al. | |
| 5,849,834 A | 12/1998 | Matsuzaki et al. | |
| 5,916,541 A | 6/1999 | Stewart | |
| 2005/0015895 A1 | 1/2005 | Azizova | |
| 2006/0159637 A1* | 7/2006 | Meyer ............... | A61K 8/29 424/59 |
| 2006/0188459 A1 | 8/2006 | Heinrichs | |
| 2006/0293197 A1 | 12/2006 | Uehara et al. | |
| 2007/0077292 A1 | 4/2007 | Pinsky | |
| 2008/0199526 A1 | 8/2008 | Poschalko et al. | |
| 2008/0317795 A1* | 12/2008 | Traynor ............... | A61Q 19/10 424/401 |
| 2009/0281056 A1 | 11/2009 | Mori et al. | |
| 2010/0239695 A1 | 9/2010 | Vielhaber et al. | |
| 2011/0250276 A1 | 10/2011 | Fournial et al. | |
| 2011/0274632 A1 | 11/2011 | Ishitobi et al. | |
| 2013/0095151 A1 | 4/2013 | Jawale et al. | |
| 2013/0131188 A1 | 5/2013 | Beckedahl et al. | |
| 2013/0319449 A1 | 12/2013 | Xavier et al. | |
| 2014/0352710 A1 | 12/2014 | Ardila | |
| 2016/0331661 A1* | 11/2016 | Masuno ............... | A61Q 19/10 |
| 2017/0056315 A1 | 3/2017 | Gevgilili et al. | |

(Continued)

FOREIGN PATENT DOCUMENTS

| | | | | |
|---|---|---|---|---|
| CN | 1286280 A | * | 3/2001 | ............ C08J 3/12 |
| CN | 1286280 A | | 3/2001 | |
| CN | 101395202 A | | 3/2009 | |

(Continued)

OTHER PUBLICATIONS

Notice of Reasons for Refusal dated Jun. 7, 2021, in corresponding JP Application No. 2017-115764, filed on Jun. 13, 2017, 25 pages.
Third Party Observation dated Feb. 1, 2021, in corresponding JP Application No. 2017-115764, filed on Jun. 13, 2017, 16 pages.
Akagi, T., et al., "Stabilization of Polyion Complex Nanoparticles Composed of Poly(amino acid) Using Hydrophobic Interactions," Langmuir 26(4):2406-2413, 2010.
Hsieh, Y.-H., et al., "Shell and Core Cross-Linked poly(L-lysine)/poly(acrylic acid) Complex Micelles," Soft Matter 10:9568-9576, 2014.
Insua, I., et al., "Polyion Complex (PIC) Particles: Preparation and Biomedical Applications," European Polymer Journal 81:198-215, 2016.

(Continued)

*Primary Examiner* — Gina C Justice
(74) *Attorney, Agent, or Firm* — CHRISTENSEN O'CONNOR JOHNSON KINDNESS PLLC

(57) ABSTRACT

The present invention relates to a composition, preferably a cosmetic composition, and more preferably a skin cosmetic composition, comprising: (a) at least one particle, comprising at least one cationic polymer and at least one anionic polymer, at least one cationic polymer and at least one amphoteric polymer, at least one anionic polymer and at least one amphoteric polymer, or at least one amphoteric polymer, and at least one non-polymeric acid having two or more pKa values or salt(s) thereof or at least one non-polymeric base having two or more pKb values or salt(s) thereof; (b) at least one oil; and (c) water. The composition according to the present invention is stable, and can have a variety of cosmetic functions. For example, the composition according to the present invention can prepare a film which can have cosmetic effects such as moisturizing due to the oil(s).

21 Claims, 1 Drawing Sheet

(56) References Cited

U.S. PATENT DOCUMENTS

| | | | |
|---|---|---|---|
| 2018/0369080 A1 | 12/2018 | Kasai et al. | |
| 2018/0369106 A1 | 12/2018 | Kasai et al. | |

FOREIGN PATENT DOCUMENTS

| | | | |
|---|---|---|---|
| CN | 101987078 A | 3/2011 | |
| CN | 101987080 A | 3/2011 | |
| CN | 103491822 A | 1/2014 | |
| CN | 104010525 A | 8/2014 | |
| EP | 0795318 A2 | 9/1997 | |
| EP | 2711050 A1 | 3/2014 | |
| EP | 2921164 A1 | 9/2015 | |
| JP | 09301824 A | 11/1997 | |
| JP | 10-175827 A | 6/1998 | |
| JP | 2004-269418 A | 9/2004 | |
| JP | 2005-036190 A | 2/2005 | |
| JP | 2005206573 A | 8/2005 | |
| JP | 2006-169410 A | 6/2006 | |
| JP | 2007161597 A | 6/2007 | |
| JP | 2008-137971 A | 6/2008 | |
| JP | 2008-273881 A | 11/2008 | |
| JP | 2008-280407 A | 11/2008 | |
| JP | 2009-510168 A | 3/2009 | |
| JP | 2011032249 A | 2/2011 | |
| JP | 2011162459 A | 8/2011 | |
| JP | 2013-056846 A | 3/2013 | |
| JP | 2013056846 A | 3/2013 | |
| JP | 2014076971 A | 5/2014 | |
| JP | 2014091708 A | 5/2014 | |
| JP | 2014114272 A | 6/2014 | |
| JP | 2014-227389 A | 12/2014 | |
| JP | 2015-101939 A | 6/2015 | |
| JP | 2015-107939 A | 6/2015 | |
| JP | 2015-127314 A | 7/2015 | |
| JP | 2015127314 A | 7/2015 | |
| JP | 6812100 B | 1/2021 | |
| JP | 6921476 B | 8/2021 | |
| KR | 0453101 B1 | 12/2004 | |
| KR | 20070077851 A1 | 7/2007 | |
| KR | 1020130119586 A | 11/2013 | |
| KR | 10-2014-0080467 A | 6/2014 | |
| KR | 20150121719 A | 10/2015 | |
| WO | 03/011239 A2 | 2/2003 | |
| WO | 2007/041627 A1 | 4/2007 | |
| WO | 2008/101546 A1 | 8/2008 | |
| WO | 2008/126971 A1 | 10/2008 | |
| WO | 2011/016363 A1 | 2/2011 | |
| WO | 2011016363 A1 | 2/2011 | |
| WO | 2013/153678 A | 10/2013 | |
| WO | 2013/153678 A1 | 10/2013 | |
| WO | 2013/174921 A1 | 11/2013 | |
| WO | 2014/063662 A1 | 5/2014 | |
| WO | 2014/132261 A2 | 9/2014 | |
| WO | 2015166459 A1 | 11/2015 | |
| WO | 2017/104221 A1 | 6/2017 | |
| WO | 2017/104585 A1 | 6/2017 | |
| WO | 2017104221 A1 | 6/2017 | |
| WO | 2017104585 A1 | 6/2017 | |

OTHER PUBLICATIONS

International Search Report and Written Opinion dated Oct. 18, 2018, issued in corresponding International Application No. PCT/JP2018/022819, filed Jun. 8, 2018, 3 pages.
Park, S.Y., et al., "Biopolymer Composite Films Based on κ-Carrageenan and Chitosan," Materials Research Bulletin 36:511-519, 2001.
Decision of Rejection dated Jan. 31, 2022, issued in corresponding Japanese Application No. 2017-115764, filed Jan. 4, 2020, 8 pages.
Decision to Grant, dated Apr. 26, 2022 in corresponding Korean Patent Application No. 10-2021-7001334, with English Translation, 4 pages.
Shafqat et al., Development of amino-functionalized silica nanoparticles for efficient and rapid removal of COD from pre-treated palm oil effluent, Journal of Materials Research Technology, vol. 8(1), 2019, pp. 385-395.
Final Office Action, dated Jan. 26, 2022, in U.S. Appl. No. 16/060,896, 20 pages.
Non-Final Office Action dated Aug. 23, 2021, in U.S. Appl. No. 16/060,896, 83 pages.
Feng, X., et al., "Colloidal Complexes From Poly(vinyl amine) and Carboxymethyl Cellulose Mixtures," Langmuir 23(6):2970-2976, Mar. 2007.
Isieh, Y.-H., et al., "Shell and Core Cross-Linked Poly(L-lysine)/Poly(acrylic acid) Complex Micelles," Soft Matter 10( 4 7):9568-9576, Dec. 2014.
International Search Report dated Mar. 13, 2017, issued in corresponding International Application No. PCT/JP2016/086831, filed Dec. 6, 2016, 3 pages.
Muller, M., et al., "Needlelike and Spherical Polyelectrolyte Complex Nanoparticles of Poly-L-lysine) and Copolymers of Maleic Acid," Langmuir 21(1):465-469, Jan. 2005.
Sohn, M. et al., "Film thickness frequency distribution of different vehicles determines sunscreen efficacy," Journal of Biomedical Optics, 19(11):115005-1 to 115005-11, Nov. 2014.
Yuan, J. et al., "Self-assembled polyion complex micelles for sustained release of hydrophilic drug," Journal of Microencapsulation, 28(2):93-98, 2011.
Japanese Office Action, with English Translation, dated Dec. 9, 2019 in corresponding Japanese Patent Application No. 2015243896, 7 pages.
Decision to Grant, with English Translation, dated Apr. 23, 2020, for corresponding Korean Patent Application No. cg]10-2018-7016096, 5 pages.
Palmer, M.R. and Pearson, P.N., "A 23,000-Year Record of Surface Water pH and PC02 in the Western Equatorial Pacific Ocean," Science, 300:480-482, Apr. 18, 2003.
Lewis III, J.L., "Overview of Acid-Base Balance," Merck Manual Consumer Version, https://www.merckmanuals.com/home/hormonal-and-metabolic-disorders/acid-base-balance/overview-of-acid-base-balance, accessed Jun. 11, 2020, originally published Jan. 2020, pp. 1-3.
Google Translate, English Translation of W02011016363A1. Obtained from https://patents.google.com/patent/W02011016363A1/en?oq=JP_2011032249 on Jun. 11, 2020. Originally published in Japanese on Feb. 10, 2011. pp. 1-11 (Year: 2011).
Feng et al., "Polymer Dictionary," China Petrochemical Press, p. 351, Jun. 1998.
Chinese Office Action dated Jun. 11, 2020, with English Translation, in corresponding Chinese Patent Application No. 201680072083.2, 25 pages.
Nam, Y.S. et al., "Tocopheryl acetate nanoemulsions stabilized with lipid-polymer hybrid emulsifiers for effective skin delivery," Colloids and Surfaces B: Biointerfaces, 94:51-57 {2012).
Chinese Office Action dated Dec. 30, 2020, issued in corresponding Application No. 201680072083.2, 8 pages.
First Chinese Office Action dated Jun. 2, 2020, issued in Application No. 201680073128.8, filed Sep. 23, 2016, 24 pages.
Safety and Technical Standards for Cosmetics, China Food and Drug Administration, pp. 120-122, Dec. 2015.
Chouqian, X., et al., "Organic Chemistry," Sun Yat-sen University Press, p. 210, Jan. 2000.
Clarivate Analytics, English Translation of JP 2014227389 A. Obtained by examiner on Apr. 26, 2021. briginally published in Japanese on Dec. 8, 2014, pp. 1-16. {Year: 2014).
Non-Final Rejection dated Apr. 30, 2021, in corresponding U.S. Appl. No. 16/060,896, 19 pages.
Final Rejection dated Nov. 3, 2020, in corresponding U.S. Appl. No. 16/060,896, 29 pages.
Non-Final Rejection dated Jun. 18, 2020, in corresponding U.S. Appl. No. 16/060,896, 26 pages.
Advisory Action dated May 1, 2020, in corresponding U.S. Appl. No. 16/060,896, 9 pages.
Final Rejection dated Feb. 28, 2020, in corresponding U.S. Appl. No. 16/060,896, 22 pages.
Non-Final Rejection dated Nov. 19, 2019, in corresponding U.S. Appl. No. 16/060,896, 20 pages.

(56) References Cited

OTHER PUBLICATIONS

Restriction Requirement dated Aug. 13, 2019, in corresponding U.S. Appl. No. 16/060,896, 9 pages.
Insua, I. et al., "Polyion complex (PIG) particles: Preparation and biomedical applications," European Polymer Journal, 81:198-215, 2016.
Hawley's Condensed Chemical Dictionary (16th Edition), published 2016; pp. 34, 35, and 1130.
Korean Notice of Grounds of Rejection dated Apr. 26, 2020, in corresponding KR Application No. 10-2018-7016486, filed Jun. 11, 2018, 17 pages.
Third Party Observation dated Jul. 6, 2020, for corresponding Japanese Patent Application No. 2015-243895, filed Dec. 15, 2015, 19 pages.
Akagi, T., et al., "Stabilization of Polyion Complex Nanoparticles Composed of Poly(amino acid) Using Hydrophobic Interactions," Langmuir 26(4):2406-2413, Feb. 2010.
Belscak-Cvitanovic, A., et al., "Encapsulation of Polyphenolic Antioxidants From Medicinal Plant Extracts in Alginate-Chitosan System Enhanced With Ascorbic Acid by Electrostatic Extrusion," Food Research International 44(4):1094-1101, May 2011.
Ichikawa, S., et al., "Formation of Biocompatible Nanoparticles by Self-Assembly of Enzymatic Hydrolysates of Chitosan and Carboxymethyl Cellulose," Bioscience, Biotechnology, and Biochemistry 69(9):1637-1642, Sep. 2005.
International Search Report dated Dec. 1, 2016, issued in corresponding International Application No. PCT/JP2016/078963, filed Sep. 23, 2016, 4 pages.
Luo, Y., et al., "Preparation and Drug Controlled-Release of Polyion Complex Micelles as Drug Delivery Systems," Colloids and Surfaces B: Biointerfaces 68(2):218-224, Feb. 2009.
Luo, Y., et al., "Preparation, Characterization and Drug Release Behavior of Polyion Complex Micelles," International Journal of Pharmaceutics 374(1-2):139-144, Jun. 2009.
Park, SY., et al., "Biopolymer Composite Films Based on κ-Carrageenan and Chitosan," Materials Research Bulletin 36(3-4):511-519, Feb.-Mar. 2001.
Non-Final Rejection dated Oct. 27, 2022, issued in corresponding U.S. Appl. No. 16/619,887, filed Dec. 5, 2019, 12 pages.
Decision of Rejection dated Jan. 31, 2022, issued in corresponding JP Application No. 2017-115764, filed Jun. 13, 2017, 8 pages.
Notice of Reasons for Refusal dated Jun. 7, 2021, issued in corresponding JP Application No. 2017-115764, filed Jun. 13, 2017, 25 pages.
Final Office Action dated Sep. 6, 2022 in corresponding U.S. Appl. No. 16/619,899, filed Dec. 5, 2019, 27 pages.
Polyquatemiurn-61—Surfactant—SAAPedia—Surfactant Technology Platform. Accessed at www.saapedia.org/en/saa/?fYpe=detail&id=3773 on Aug. 26, 2022, 3 pages.
Decision to Grant, dated Apr. 25, 2022 in corresponding Korean Patent Application No. 10-2021-7001334, with English Translation, 4 pages.
Non-Final Office Action dated Apr. 20, 2022 in corresponding U.S. Appl. No. 16/619,899, filed Dec. 5, 2019, 39 pages.
Final Office Action dated Aug. 25, 2021, from U.S. Appl. No. 16/062,065, filed Jun. 13, 2018, 18 pages.
Mexoryl SX, PubChem CID 6442003, <https://pubchem.ncbLnlm.nih.gov/compound/Mexoryl-SX?orm=MY01SV&OCID=MY01SV> [retrieved Oct. 21, 2021), 32 pages_.
Japanese Office Aclion, dated Sep. 13, 2021, in oorresponding Japanese Palenl Applicalion No. 2017-115767, With English Translation. 10 pages.
Japanese Office Action, dated Oct. 18, 2021. in corresponding Japanese Patent Application No. 2017-115767. with English Translation, 13 pages.
Third Party Observation mailed Feb. 1, 2021, issued in corresponding Japanese Application No. JP2017-115767, filed on Jun. 13, 2017, 14 pages.
Google Patents. English Translation of JP2015107939A. Obtained from https://patents.google.com/patent/JP2015107939A/en?oq=JP+2015-107939 on Sep. 14, 2020. Originally published in Japanese on Jun. 11, 2015, 17 printed pages. (Year: 2015).
Anonymous, "Kose Sekkisei Emulsion Day Essence SPF25/PA+", Aug. 12, 2010, pp. 1-3, obtained from the website: http://www.cosdna.com/chs/cosmetic_c03838037.html.
Office Action dated Oct. 10, 2019 in U.S. Appl. No. 16/062,065.
Office Action dated Jun. 7, 2021, in U.S. Appl. No. 16/062,065, 13 pages.
International Search Report dated Oct. 18, 2018 in PCT Application No. PCT/JP2018/023047, 4 pages.
Office Action dated Sep. 21, 2020, in U.S. Appl. No. 16/619,899, 27 pages.
Office Action dated May 17, 2021, in U.S. Appl. No. 16/619,899, 29 pages.
Office Action dated Apr. 20, 2022, in U.S. Appl. No. 16/619,899, 39 pages.
Final Office Action dated Sep. 6, 2022, in U.S. Appl. No. 16/619,899, 26 pages.
Notice of Allowance dated Oct. 6, 2022, in U.S. Appl. No. 16/060,896, 14 pages.

\* cited by examiner

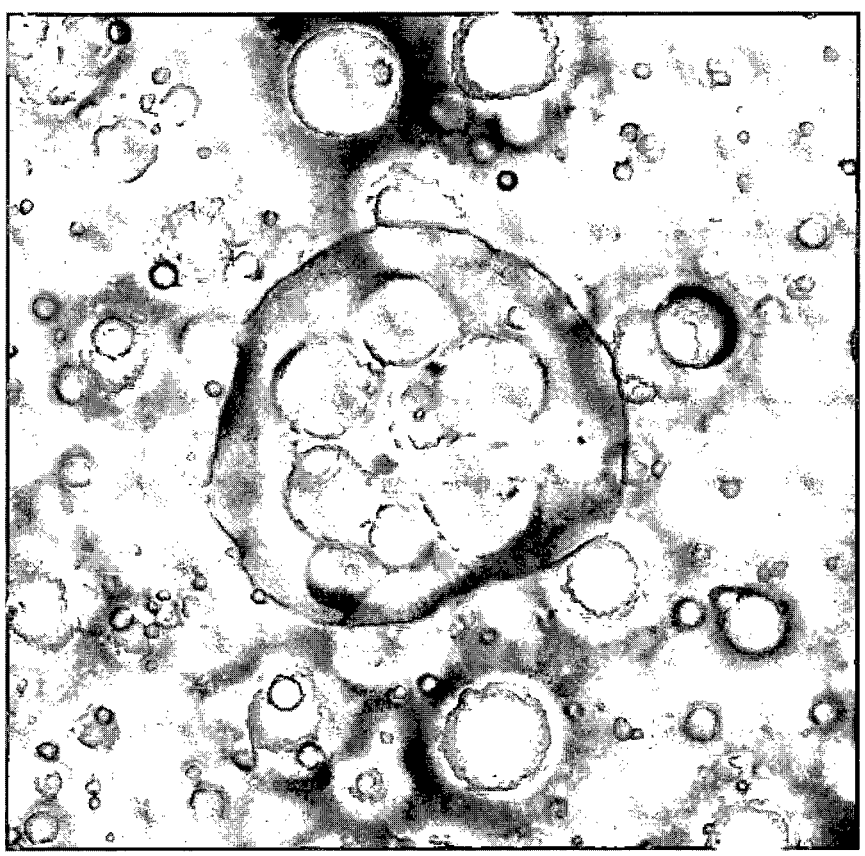

COMPOSITION COMPRISING POLYION COMPLEX PARTICLE AND OIL

TECHNICAL FIELD

The present invention relates to a composition including polyion complex particles and a film of polyion complex particles, as well as a process for preparing a film by using polyion complex particles and a use of polyion complex particles for preparing a film.

BACKGROUND ART

A polyion complex which is formed with an anionic polymer and a cationic polymer has already been known.

The use of a film made from a polyion complex for cosmetic purposes is also proposed by, for example, WO 2013/153678 and JP-A-2014-227389. The film disclosed in WO 2013/153678 and JP-A-2014-227389 can provide certain cosmetic effects.

However, the preparation of the film disclosed in WO 2013/153678 and JP-A-2014-227389 requires a spin coating process which needs a high speed rotation of a substrate, and therefore, it may be difficult to prepare the film in-situ on a keratin substrate such as skin.

JP-A-2015-107939 discloses the preparation of a film made from a polyion complex for cosmetic purposes by spraying a first solution of either of an anionic polymer and a cationic polymer, and spraying a second solution of the other of the anionic polymer and the cationic polymer, on a keratin substance, to mix the anionic and cationic polymers to form a film including the polyion complex. This preparation can prepare the film in-situ on a keratin substance such as skin.

However, it may be difficult to prepare the above film by the spraying process disclosed in JP-A-2015-107939 without careful control, because it may not be easy to control the amounts of the first and second solutions to be sprayed. In particular, the preparation of a relatively thick film by using the spraying process disclosed in JP-A-2015-107939 may be difficult.

One option to easily make a film made from a polyion complex may be to use a polyion complex in the form of particles. For example, JP-A-2005-36190 discloses a dispersion including polyion complex particles which has been formed by an anionic polymer and a cationic polymer.

DISCLOSURE OF INVENTION

However, it has been discovered that a dispersion including polyion complex particles is not always stable. If the dispersion is unstable, the polyion complex particles tend to precipitate.

Thus, a first objective of the present invention is to provide a stable composition, in particular a stable composition in the form of an emulsion, which includes polyion complex particles.

The above objective of the present invention can be achieved by a composition, preferably a cosmetic composition, and more preferably a skin cosmetic composition comprising:

(a) at least one particle, comprising at least one cationic polymer and at least one anionic polymer, at least one cationic polymer and at least one amphoteric polymer, at least one anionic polymer and at least one amphoteric polymer, or at least one amphoteric polymer, and at least one non-polymeric acid having two or more pKa values or salt(s) thereof or at least one non-polymeric base having two or more pKb values or salt(s) thereof;

(b) at least one oil; and (c) water.

A plurality of the (a) particles may be present at the interface between the (b) oil and the (c) water, or may form a capsule having a hollow, and the (b) oil is present in the hollow.

The cationic polymer may have at least one positively chargeable and/or positively charged moiety selected from the group consisting of a primary, secondary or tertiary amino group, a quaternary ammonium group, a guanidine group, a biguanide group, an imidazole group, an imino group, and a pyridyl group.

The cationic polymer may be selected from the group consisting of cyclopolymers of alkyldiallylamine and cyclopolymers of dialkyldiallylammonium such as (co)polydiallyldialkyl ammonium chloride, (co)polyamines such as (co)polylysines and chitosans, cationic (co)polyaminoacids such as collagen, and salts thereof.

The anionic polymer may have at least one negatively chargeable and/or negatively charged moiety selected from the group consisting of a sulfuric group, a sulfate group, a sulfonic group, a sulfonate group, a phosphoric group, a phosphate group, a phosphonic group, a phosphonate group, a carboxylic group, and a carboxylate group.

The anionic polymer may be selected from the group consisting of polysaccharides such as alginic acid, hyaluronic acid, and cellulose polymers, anionic (co)polyaminoacids such as (co)polyglutamic acids, (co)poly(meth)acrylic acids, (co)polyamic acids, (co)polystyrene sulfonate, (co)poly(vinyl sulfate), dextran sulfate, chondroitin sulfate, (co)polymaleic acids, (co)polyfumaric acids, maleic acid (co)polymers, and salts thereof.

The amphoteric polymer may have at least one positively chargeable and/or positively charged moiety selected from the group consisting of a primary, secondary or tertiary amino group, a quaternary ammonium group, a guanidine group, a biguanide group, an imidazole group, an imino group, and a pyridyl group, and at least one negatively chargeable and/or negatively charged moiety selected from the group consisting of a sulfuric group, a sulfate group, a sulfonic group, a sulfonate group, a phosphoric group, a phosphate group, a phosphonic group, a phosphonate group, a carboxylic group, and a carboxylate group.

The amphoteric polymer may be selected from the group consisting of polyquaternium-22, polyquaternium-39, polyquaternium-53, polyquaternium-64, polyquaternium-51, polyquaternium-61, and mixtures thereof.

The amount of the polymer(s), in the composition according to the present invention may be from 0.001 to 25% by weight, preferably from 0.1 to 20% by weight, and more preferably from 0.3 to 15% by weight, relative to the total weight of the composition.

The amount of the non-polymeric acid having two or more pKa values or salt(s) thereof or non-polymeric base having two or more pKb values or salt(s) thereof in the composition according to the present invention may be from 0.0001 to 30% by weight, preferably from 0.01 to 20% by weight, and more preferably from 0.1 to 15% by weight, relative to the total weight of the composition.

The (a) particle may comprise (d) at least one hydrophobic amino acid other than the non-polymeric acid or base.

The pH of the composition according to the present invention may be from 3 to 9, preferably from 3.5 to 8.5, and more preferably from 4 to 8.

The amount of the (a) particle in the composition according to the present invention may be from 0.001 to 60% by weight, preferably from 0.1 to 50% by weight, and more preferably from 1 to 40% by weight, relative to the total weight of the composition.

It is preferable that the (b) oil be selected from polar oils.

The amount of the (b) oil(s) in the composition may be from 0.01 to 50% by weight, preferably from 0.1 to 40% by weight, and more preferably from 1 to 35% by weight, relative to the total weight of the composition.

It is preferable that the composition according to the present invention be in the form of an emulsion, more preferably an O/W emulsion, and even more preferably an O/W emulsion comprising 0.1% by weight or less of surfactant(s), preferably 0.01% by weight or less of surfactant(s), and more preferably no surfactant(s).

It is preferable that the composition according to the present invention comprise (e) at least one oil gelling agent.

A second objective of the present invention is to provide a process which can easily prepare a film made from polyion complex particles wherein the film comprises at least one oil.

The above objective of the present invention can be achieved by a process for preparing a film, preferably a cosmetic film, comprising:
applying onto a substrate, preferably a keratin substrate, and more preferably skin, the composition according to the present invention; and
drying the composition.

A third objective of the present invention is to provide a film made from polyion complex particles wherein the film comprises at least one oil.

The above objective of the present invention can be achieved by:
(1) A film, preferably a cosmetic film, prepared by a process comprising:
applying onto a substrate, preferably a keratin substrate, and more preferably skin,
the composition according to the present invention; and
drying the composition,
or
(2) A film, preferably a cosmetic film, comprising:
at least one cationic polymer and at least one anionic polymer,
at least one cationic polymer and at least one amphoteric polymer,
at least one anionic polymer and at least one amphoteric polymer, or
at least one amphoteric polymer;
at least one non-polymeric acid having two or more pKa values or salt(s) thereof or
at least one non-polymeric base having two or more pKb values or salt(s) thereof;
and
at least one oil.

The present invention also relates to a cosmetic process for a keratin substrate such as skin, comprising
applying to the keratin substrate the composition according to the present invention; and drying the composition to form a cosmetic film on the keratin substrate.

The cosmetic film thus obtained can be resistant to water with a pH of 7 or less, and can be removable with water with a pH of more than 7, preferably 8 or more, and more preferably 9 or more.

The present invention also relates to a use of the composition according to the present invention for the preparation of a cosmetic film on a keratin substrate such as skin, wherein the cosmetic film is resistant to water with a pH of 7 or less, and is removable with water with a pH of more than 7, preferably 8 or more, and more preferably 9 or more.

BRIEF DESCRIPTION OF DRAWINGS

FIG. 1 shows encapsulation of oil globules by the PGP according to Example 1.

BEST MODE FOR CARRYING OUT THE INVENTION

After diligent research, the inventors have discovered that it is possible to provide a stable composition such as a stable emulsion, which includes polyion complex particles and oil(s). Thus, the composition according to the present invention comprises:
(a) at least one particle, comprising
at least one cationic polymer and at least one anionic polymer,
at least one cationic polymer and at least one amphoteric polymer,
at least one anionic polymer and at least one amphoteric polymer, or
at least one amphoteric polymer,
and
at least one non-polymeric acid having two or more pKa values or salt(s) thereof or
at least one non-polymeric base having two or more pKb values or salt(s) thereof;
(b) at least one oil; and
(c) water.

It may be preferable that a plurality of the (a) particles are present at the interface between the (b) oil and the (c) water, or a plurality of the (a) particles form a capsule having a hollow, and the (b) oil is present in the hollow.

Further, the inventors have discovered that it is possible to provide a process which can easily prepare a film comprising polyion complex particles and oil(s). Thus, the process according to the present invention is a process for preparing a film, preferably a cosmetic film, the process comprising
applying onto a substrate, preferably a keratin substrate, the composition according to the present invention; and
drying the composition.

Furthermore, the inventors have discovered that it is possible to provide a film comprising polyion complex particles and oil(s). Thus, the film according to the present invention is
(1) A film, preferably a cosmetic film, prepared by a process comprising:
applying onto a substrate, preferably a keratin substrate, and more preferably skin,
the composition according to the present invention; and
drying the composition,
or
(2) A film, preferably a cosmetic film, comprising:
at least one cationic polymer and at least one anionic polymer,
at least one cationic polymer and at least one amphoteric polymer, at least one anionic polymer and at least one amphoteric polymer, or at least one amphoteric polymer;

at least one non-polymeric acid having two or more pKa values or salt(s) thereof or at least one non-polymeric base having two or more pKb values or salt(s);

and at least one oil.

The composition according to the present invention is stable for a long period of time, and can be used to easily prepare a film of a polyion complex wherein the film includes at least one oil by applying the composition onto a substrate, preferably a keratin substrate such as skin and hair, and more preferably skin, and drying the composition.

The polyion complex film according to the present invention can have a variety of cosmetic functions.

For example, the film according to the present invention itself may have cosmetic effects such as moisturizing due to the oil(s), as well as absorbing or adsorbing malodor, changing the appearance of a keratin substrate such as skin, changing the feel to the touch of the keratin substrate, and/or protecting the keratin substrate from, for example, dirt or pollutants.

It is also possible to realize sustained release of the oil(s) from the film.

If the polyion complex film includes at least one cosmetic active ingredient other than the oil(s), the film can have cosmetic effects provided by the cosmetic active ingredient(s). For example, if the polyion complex film includes at least one cosmetic active ingredient selected from UV filters, anti-aging agents, anti-sebum agents, deodorant agents, anti-perspirant agents, whitening agents and a mixture thereof, the film can filter UV rays, treat the aging of the skin, absorb sebum on the skin, control odors on the skin, control the perspiration on the skin, and/or whiten the skin.

The film according to the present invention may be transparent, and therefore, may not be easy to perceive, even when the film is relatively thick.

Further, the film according to the present invention is water-resistant, and therefore, it can remain on a keratin substrate such as skin even if the surface of the keratin substrate is wet due to, for example sweat and rain.

Furthermore, the film according to the present invention can be easily removed from a keratin substrate such as skin under alkaline conditions. Therefore, the film according to the present invention is difficult to remove with water, while it can be easily removed with a soap which can provide alkaline conditions.

Thus, if the film according to the present invention includes a hydrophilic or water-soluble UV filter, the film according to the present invention can show UV shielding effects which are resistant to water (water-proof) and can be long-lasting, but can be easily removed with a soap which can provide alkaline conditions.

Hereinafter, the composition, process, film and the like according to the present invention will be explained in a more detailed manner.

[Polyion Complex Particle]

The composition according to the present invention includes (a) at least one particle which is a polyion complex particle. Two or more different types of (a) particles may be used in combination. Thus, a single type of (a) particle or a combination of different types of (a) particles may be used.

The size of the polyion complex particle may be from 5 nm to 100 µm, preferably from 100 nm to 50 µm, more preferably from 200 nm to 30 µm, and even more preferably from 500 nm to 20 µm. A particle size less than 1 µm can be measured by a dynamic light scattering method, and a particle size more than 1 µm can be measured by an optical microscope. This particle size may be based on number average diameter.

The amount of the (a) particle(s) in the composition according to the present invention may be 0.001% by weight or more, preferably 0.1% by weight or more, and more preferably 1% by weight or more, relative to the total weight of the composition.

The amount of the (a) particle(s) in the composition according to the present invention may be 60% by weight or less, preferably 50% by weight or less, and more preferably 40% by weight or less, relative to the total weight of the composition.

The amount of the (a) particle(s) in the composition according to the present invention may be from 0.001 to 60% by weight, preferably from 0.1 to 50% by weight, and more preferably from 1 to 40% by weight, relative to the total weight of the composition.

A plurality of the (a) particles can be present at the interface between the (b) oil and the (c) water. Thus, the (a) particles can form an emulsion. For example, if the (c) water constitutes a continuous phase and the (b) oil constitutes dispersed phases, the (a) particles can form an O/W emulsion which may be similar to a so-called Pickering emulsion.

Alternatively, a plurality of the (a) particles can form a capsule having a hollow. The (b) oil can be present in the hollow. In other words, the (b) oil can be incorporated into the capsule. The wall of the capsule may be composed of a continuous layer or film formed from the (a) particles. While not wishing to be bound by theory, it is believed that the (a) particles can re-organize at the interface of the (b) oil and the (c) water to spontaneously form a capsule having a hollow to include the (b) oil. For example, a continuous phase constituted with the (c) water and a dispersed phases constituted with the (b) oil in the capsule can form an O/W emulsion which may also be similar to a so-called Pickering emulsion.

The above would mean that the (a) particle itself is amphiphilic and insoluble in oil or water.

The (a) particle includes at least one polymer or a combination of polymers. Specifically, the (a) particle includes:

(1) at least one cationic polymer and at least one anionic polymer;

(2) at least one cationic polymer and at least one amphoteric polymer;

(3) at least one anionic polymer and at least one amphoteric polymer; or (4) at least one amphoteric polymer.

There is no limit to the type of the cationic, anionic and amphoteric polymers. Two or more different types of cationic polymers may be used in combination. Thus, a single type of cationic polymer or a combination of different types of cationic polymers may be used. Two or more different types of anionic polymers may be used in combination. Thus, a single type of anionic polymer or a combination of different types of anionic polymers may be used.

Two or more different types of amphoteric polymers may be used in combination. Thus, a single type of amphoteric polymer or a combination of different types of amphoteric polymers may be used.

In the above (1), the ratio of the amount, for example chemical equivalent, of the cationic polymer(s)/the anionic polymer(s) may be 0.05-18, preferably 0.1-10, and more preferably 0.5-5.0. In particular, it may be preferable that the number of the cationic groups of the cationic polymer(s)/the number of anionic groups of the anionic polymer(s) be 0.05-18, more preferably 0.1-10, and even more preferably 0.5-5.0.

In the above (2), the ratio of the amount, for example chemical equivalent, of the cationic polymer(s)/the amphoteric polymer(s) may be 0.05-18, preferably 0.1-10, and more preferably 0.5-5.0. In particular, it may be preferable that the number of the cationic groups of the cationic polymer(s)/the number of cationic and anionic groups of the amphoteric polymer(s) be 0.05-18, more preferably 0.1-10, and even more preferably 0.5-5.0.

In the above (3), the ratio of the amount, for example chemical equivalent, of the anionic polymer(s)/the amphoteric polymer(s) may be 0.05-18, preferably 0.1-10, and more preferably 0.5-5.0. In particular, it may be preferable that the number of the anionic groups of the anionic polymer(s)/the number of cationic and anionic groups of the amphoteric polymer(s) be 0.05-18, more preferably 0.1-10, and even more preferably 0.5-5.0.

The total amount of the polymer(s) according to any one of the above (1) to (4) in the composition according to the present invention may be 0.001% by weight or more, preferably 0.1% by weight or more, and more preferably 1% by weight or more, relative to the total weight of the composition.

The total amount of the polymer(s) according to any one of the above (1) to (4) in the composition according to the present invention may be 25% by weight or less, preferably 20% by weight or less, and more preferably 15% by weight or less, relative to the total weight of the composition.

The total amount of the polymer(s) according to any one of the above (1) to (4) in the composition according to the present invention may be from 0.001 to 25% by weight, preferably from 0.1 to 20% by weight, and more preferably from 1 to 15% by weight, relative to the total weight of the composition.

(Cationic Polymer)

A cationic polymer has a positive charge density. The charge density of the cationic polymer may be from 0.01 meq/g to 20 meq/g, preferably from 0.05 to 15 meq/g, and more preferably from 0.1 to 10 meq/g.

It may be preferable that the molecular weight of the cationic polymer be 500 or more, preferably 1000 or more, more preferably 2000 or more, and even more preferably 5000 or more.

Unless otherwise defined in the descriptions, "molecular weight" means a number average molecular weight.

The cationic polymer may have at least one positively chargeable and/or positively charged moiety selected from the group consisting of a primary, secondary or tertiary amino group, a quaternary ammonium group, a guanidine group, a biguanide group, an imidazole group, an imino group, and a pyridyl group. The term (primary) "amino group" here means a group of —NH$_2$.

The cationic polymer may be a homopolymer or a copolymer. The term "copolymer" is understood to mean both copolymers obtained from two kinds of monomers and those obtained from more than two kinds of monomers, such as terpolymers obtained from three kinds of monomers.

The cationic polymer may be selected from natural and synthetic cationic polymers. Non-limiting examples of the cationic polymers are as follows:

(1) Homopolymers and copolymers derived from acrylic or methacrylic esters and amides and comprising at least one unit chosen from units of the following formulas:

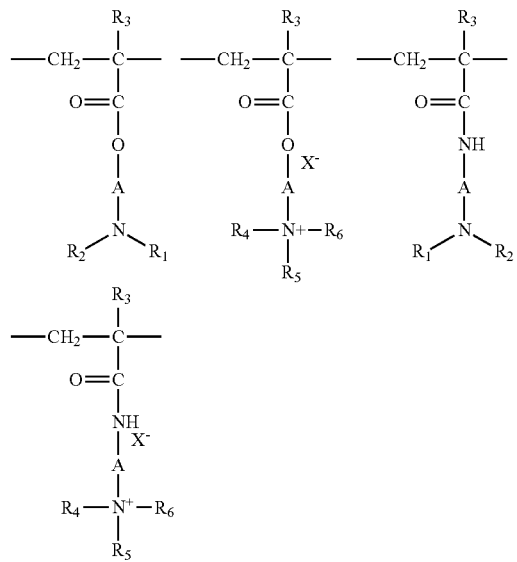

wherein:
R$_1$ and R$_2$, which may be identical or different, are chosen from hydrogen and alkyl groups comprising from 1 to 6 carbon atoms, for instance, methyl and ethyl groups;

R$_3$, which may be identical or different, is chosen from hydrogen and CH$_3$;

the symbols A, which may be identical or different, are chosen from linear or branched alkyl groups comprising from 1 to 6 carbon atoms, for example, from 2 to 3 carbon atoms and hydroxyalkyl groups comprising from 1 to 4 carbon atoms;

R$_4$, R$_5$, and R$_6$, which may be identical or different, are chosen from alkyl groups comprising from 1 to 18 carbon atoms and benzyl groups, and in at least one embodiment, alkyl groups comprising from 1 to 6 carbon atoms; and X is an anion derived from an inorganic or organic acid, such as methosulphate anions and halides, for instance chloride and bromide.

The copolymers of family (1) may also comprise at least one unit derived from comonomers which may be chosen from acrylamides, methacrylamides, diacetone acrylamides, acrylamides and methacrylamides substituted on the nitrogen atom with (C$_1$-C$_4$) lower alkyl groups, groups derived from acrylic or methacrylic acids and esters thereof, vinyllactams such as vinylpyrrolidone and vinylcaprolactam, and vinyl esters.

Examples of copolymers of family (1) include, but are not limited to:

copolymers of acrylamide and of dimethylaminoethyl methacrylate quaternized with dimethyl sulphate or with a dimethyl halide, copolymers of acrylamide and of methacryloyloxyethyltrimethylammonium chloride described, for example, in European Patent Application No. 0 080 976, copolymers of acrylamide and of methacryloyloxyethyltrimethylammonium methosulphate, quaternized or nonquaternized vinylpyrrolidone/dialkylaminoalkyl acrylate or methacrylate copolymers, described, for example, in French Patent Nos. 2 077 143 and 2 393 573, dimethylaminoethyl methacrylate/vinylcaprolactam/vinylpyrrolidone terpolymers, vinylpyrrolidone/methacrylamidopropyldimethylamine copolymers, quaternized vinylpyrrolidone/dimethylaminopropylmethacrylamide copolymers, and crosslinked methacryloyloxy($C_1$-$C_4$)alkyltri($C_1$-$C_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with a compound containing an olefinic unsaturation, for example, methylenebisacrylamide.

(2) Cationic cellulose derivatives such as cellulose ether derivatives comprising quaternary ammonium groups described, for example, in French Patent No. 1 492 597, such as the polymers sold under the names "JR" (JR 400, JR 125, JR 30M) or "LR" (LR 400, LR 30M) by the company Union Carbide Corporation. These polymers are also defined in the CTFA dictionary as quaternary ammoniums of hydroxyethylcellulose that have reacted with an epoxide substituted with a trimethylammonium group.

(3) Cationic cellulose derivatives such as cellulose copolymers and cellulose derivatives grafted with a water-soluble monomer of quaternary ammonium, and described, for example, in U.S. Pat. No. 4,131,576, such as hydroxyalkylcelluloses, for instance, hydroxymethyl-, hydroxyethyl-, and hydroxypropylcelluloses grafted, for example, with a salt chosen from methacryloylethyltrimethylammonium, methacrylamidopropyltrimethylammonium, and dimethyldiallylammonium salts.

Commercial products corresponding to these polymers include, for example, the products sold under the name "Celquat® L 200" and "Celquat® H 100" by the company National Starch.

(4) Non-cellulose-based cationic polysaccharides described in U.S. Pat. Nos. 3,589,578 and 4,031,307, such as guar gums comprising cationic trialkylammonium groups, cationic hyaluronic acid, and dextran hydroxypropyl trimonium chloride. Guar gums modified with a salt, for example the chloride, of 2,3-epoxypropyltrimethylammonium (guar hydroxypropyltrimonium chloride) may also be used.

Such products are sold, for instance, under the trade names JAGUAR® C13 S, JAGUAR® C15, JAGUAR® C17, and JAGUAR® C162 by the company MEYHALL.

(5) Polymers comprising piperazinyl units and divalent alkylene or hydroxyalkylene groups comprising straight or branched chains, optionally interrupted with at least one entity chosen from oxygen, sulphur, nitrogen, aromatic rings, and heterocyclic rings, and also the oxidation and/or quaternization products of these polymers. Such polymers are described, for example, in French Patent Nos. 2.162 025 and 2 280 361.

(6) Water-soluble polyamino amides prepared, for example, by polycondensation of an acidic compound with a polyamine; these polyamino amides possibly being crosslinked with an entity chosen from epihalohydrins; diepoxides; dianhydrides; unsaturated dianhydrides; bisunsaturated derivatives; bishalohydrins; bisazetidiniums; bishaloacyidiamines; bisalkyl halides; oligomers resulting from the reaction of a difunctional compound which is reactive with an entity chosen from bishalohydrins, bisazetidiniums, bishaloacyldiamines, bisalkyl halides, epihalohydrins, diepoxides, and bisunsaturated derivatives; the crosslinking agent being used in an amount ranging from 0.025 to 0.35 mol per amine group of the polyamino amide; these polyamino amides optionally being alkylated or, if they comprise at least one tertiary amine function, they may be quaternized. Such polymers are described, for example, in French Patent Nos. 2 252 840 and 2 368 508.

(7) Polyamino amide derivatives resulting from the condensation of polyalkylene polyamines with polycarboxylic acids, followed by alkylation with difunctional agents, for example, adipic acid/dialkylaminohydroxyalkyldialkylenetriamine polymers in which the alkyl group comprises from 1 to 4 carbon atoms, such as methyl, ethyl, and propyl groups, and the alkylene group comprises from 1 to 4 carbon atoms, such as an ethylene group. Such polymers are described, for instance, in French Patent No. 1 583 363. In at least one embodiment, these derivatives may be chosen from adipic acid/dimethylaminohydroxypropyldiethylenetriamine polymers.

(8) Polymers obtained by reaction of a polyalkylene polyamine comprising two primary amine groups and at least one secondary amine group, with a dicarboxylic acid chosen from diglycolic acid and saturated aliphatic dicarboxylic acids comprising from 3 to 8 carbon atoms. The molar ratio of the polyalkylene polyamine to the dicarboxylic acid may range from 0.8:1 to 1.4:1; the polyamino amide resulting therefrom being reacted with epichlorohydrin in a molar ratio of epichlorohydrin relative to the secondary amine group of the polyamino amide ranging from 0.5:1 to 1.8:1. Such polymers are described, for example, in U.S. Pat. Nos. 3,227,615 and 2,961,347.

(9) Cyclopolymers of alkyldiallylamine and cyclopolymers of dialkyldiallyl-ammonium, such as homopolymers and copolymers comprising, as the main constituent of the chain, at least one unit chosen from units of formulas (Ia) and (Ib):

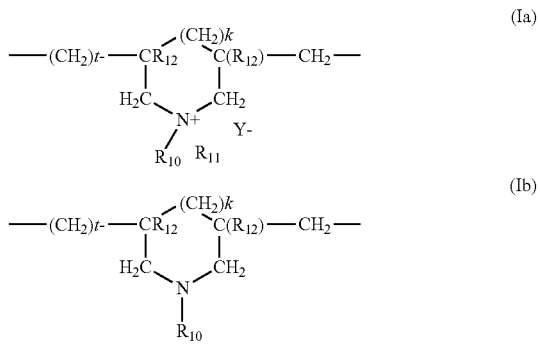

wherein:
k and t, which may be identical or different, are equal to 0 or 1, the sum k+t being equal to 1; $R_{12}$ is chosen from hydrogen and methyl groups;
$R_{10}$ and $R_{11}$, which may be identical or different, are chosen from alkyl groups comprising from 1 to 6 carbon atoms, hydroxyalkyl groups in which the alkyl group comprises, for example, from 1 to 5 carbon atoms, and lower ($C_1$-$C_4$)amidoalkyl groups, or $R_{10}$ and $R_{11}$ may form, together with the nitrogen atom to which they are attached, heterocyclic groups such as piperidinyl and morpholinyl; and
Y' is an anion such as bromide, chloride, acetate, borate, citrate, tartrate, bisulphate, bisulphite, sulphate, and phosphate. These polymers are described, for example, in French Patent No. 2 080 759 and in its Certificate of Addition 2 190 406.

In one embodiment, $R_{10}$ and $R_{11}$, which may be identical or different, are chosen from alkyl groups comprising from 1 to 4 carbon atoms.

Examples of such polymers include, but are not limited to, (co)polydiallyldialkyl ammonium chloride such as the dimethyidiallylammonium chloride homopolymer sold under the name "MERQUAT® 100" by the company CALGON (and its homologues of low weight-average molecular mass) and the copolymers of diallyldimethylammonium chloride and of acrylamide sold under the name "MERQUAT® 550".

Quaternary diammonium polymers comprising at least one repeating unit of formula (II):

(II)

wherein:
$R_{13}$, $R_{14}$, $R_{15}$, and $R_{16}$, which may be identical or different, are chosen from aliphatic, alicyclic, and arylaliphatic groups comprising from 1 to 20 carbon atoms and lower hydroxyalkyl aliphatic groups, or alternatively $R_{13}$, $R_{14}$, $R_{15}$, and $R_{16}$ may form, together or separately, with the nitrogen atoms to which they are attached, heterocycles optionally comprising a second heteroatom other than nitrogen, or alternatively $R_{13}$, $R_{14}$, $R_{15}$, and $R_{16}$, which may be identical or different, are chosen from linear or branched $C_1$-$C_6$ alkyl groups substituted with at least one group chosen from nitrile groups, ester groups, acyl groups, amide groups, —CO—O—$R_{17}$-E groups, and —CO—NH—$R_{17}$-E groups, wherein $R_{17}$ is an alkylene group and E is a quaternary ammonium group;

$A_1$ and $B_1$, which may be identical or different, are chosen from polymethylene groups comprising from 2 to 20 carbon atoms, which may be linear or branched, saturated or unsaturated, and which may comprise, linked or intercalated in the main chain, at least one entity chosen from aromatic rings, oxygen, sulphur, sulphoxide groups, sulphone groups, disulphide groups, amino groups, alkylamino groups, hydroxyl groups, quaternary ammonium groups, ureido groups, amide groups, and ester groups, and $X^-$ is an anion derived from an inorganic or organic acid;
$A_1$, $R_{13}$, and $R_{15}$ may form, together with the two nitrogen atoms to which they are attached, a piperazine ring;
if $A_1$ is chosen from linear or branched, saturated or unsaturated alkylene or hydroxyalkylene groups, $B_1$ may be chosen from:

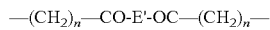

wherein E' is chosen from:
a) glycol residues of formula —O—Z—O—, wherein Z is chosen from linear or branched hydrocarbon-based groups and groups of the following formulas:

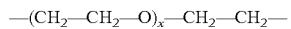

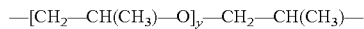

wherein x and y, which may be identical or different, are chosen from integers ranging from 1 to 4, which represent a defined and unique degree of polymerization, and numbers ranging from 1 to 4, which represent an average degree of polymerization;
b) bis-secondary diamine residue such as piperazine derivatives;

c) bis-primary diamine residues of formula —NH—Y—NH—, wherein Y is chosen from linear or branched hydrocarbon-based groups and the divalent group —$CH_2$—$CH_2$—S—S—$CH_2$—$CH_2$—; and
d) ureylene groups of formula —NH—CO—NH—.

In at least one embodiment, $X^-$ is an anion such as chloride or bromide.

Polymers of this type are described, for example, in French Patent Nos. 2 320 330; 2 270 846; 2 316 271; 2 336 434; and 2 413 907 and U.S. Pat. Nos. 2,273,780; 2,375,853; 2,388,614; 2,454,547; 3,206,462; 2,261,002; 2,271,378; 3,874,870; 4,001,432; 3,929,990; 3,966,904; 4,005,193; 4,025,617; 4,025,627; 4,025,653; 4,026,945; and 4,027,020.

Non-limiting examples of such polymers include those comprising at least one repeating unit of formula (III):

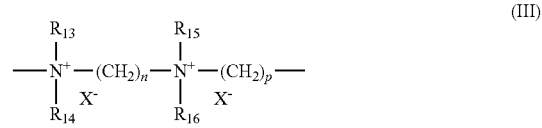

(III)

wherein $R_{13}$, $R_{14}$, $R_{15}$, and $R_{16}$, which may be identical or different, are chosen from alkyl and hydroxyalkyl groups comprising from 1 to 4 carbon atoms, n and p, which may be identical or different, are integers ranging from 2 to 20, and $X^-$ is an anion derived from an inorganic or organic acid.

(11) Polyquaternary ammonium polymers comprising units of formula (IV):

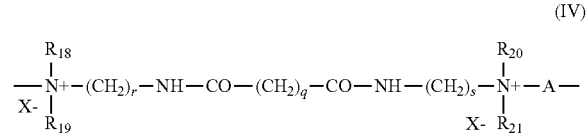

(IV)

wherein:
$R_{18}$, $R_{19}$, $R_{20}$, and $R_{21}$, which may be identical or different, are chosen from hydrogen, methyl groups, ethyl groups, propyl groups, β-hydroxyethyl groups, β-hydroxypropyl groups, —$CH_2CH_2(OCH_2CH_2)_p$OH groups, wherein p is chosen from integers ranging from 0 to 6, with the proviso that $R_{18}$, $R_{19}$, $R_{20}$, and $R_{21}$ are not simultaneously hydrogen,
r and s, which may be identical or different, are chosen from integers ranging from 1 to 6,
q is chosen from integers ranging from 0 to 34,
$X^-$ is an anion such as a halide, and
A is chosen from radicals of dihalides and —$CH_2$—$CH_2$—O—$CH_2$—$CH_2$—.

Such compounds are described, for instance, in European Patent Application No. 0 122 324.

(12) Quaternary polymers of vinylpyrrolidone and of vinylimidazole.

Other examples of suitable cationic polymers include, but are not limited to, cationic proteins and cationic protein hydrolysates, polyalkyleneimines, such as polyethyleneimines, polymers comprising units chosen from vinylpyridine and vinylpyridinium units, condensates of polyamines and of epichlorohydrin, quaternary polyureylenes, and chitin derivatives.

According to one embodiment of the present invention, the at least one cationic polymer is chosen from cellulose ether derivatives comprising quaternary ammonium groups, such as the products sold under the name "JR 400" by the company UNION CARBIDE CORPORATION, cationic cyclopolymers, for instance, the homo-polymers and copolymers of dimethyldiallylammonium chloride sold under the names MERQUAT® 100, MERQUAT® 550, and MERQUAT® S by the company CALGON, guar gums modified with a 2,3-epoxypropyltrimethylammonium salt, and quaternary polymers of vinylpyrrolidone and of vinylimidazole.

(13) Polyamines

As the cationic polymer, it is also possible to use (co)polyamines, which may be homopolymers or copolymers, with a plurality of amino groups. The amino group may be a primary, secondary, tertiary or quaternary amino group. The amino group may be present in a polymer backbone or a pendent group, if present, of the (co)polyamines.

As example of the (co)polyamines, mention may be made of chitosan, (co)polyallylamines, (co)polyvinylamines, (co)polyanilines, (co)polyvinylimidazoles, (co)polydimethylaminoethylenemethacrylates, (co)polyvinylpyridines such as (co)poly-1-methyl-2-vinylpyridines, (co)polyimines such as (co) polyethyleneimines, (co)polypyridines such as (co) poly(quaternary pyridines), (co)polybiguanides such as (co) polyaminopropyl biguanides, (co)polylysines, (co)polyornithines, (co)polyarginines, (co)polyhistidines, aminodextrans, aminocelluloses, amino(co)polyvinylacetals, and salts thereof.

As the (co)polyamines, it is preferable to use (co)polylysines. Polylysine is well known. Polylysine can be a natural homopolymer of L-lysine that can be produced by bacterial fermentation. For example, polylysine can be ε-Poly-L-lysine, typically used as a natural preservative in food products. Polylysine is a polyelectrolyte which is soluble in polar solvents such as water, propylene glycol and glycerol. Polylysine is commercially available in various forms, such as poly D-lysine and poly L-lysine. Polylysine can be in salt and/or solution form.

(14) Cationic Polyaminoacids

As the cationic polymer, it may be possible use cationic polyaminoacids, which may be cationic homopolymers or copolymers, with a plurality of amino groups and carboxyl groups. The amino group may be a primary, secondary, tertiary or quaternary amino group. The amino group may be present in a polymer backbone or a pendent group, if present, of the cationic polyaminoacids. The carboxyl group may be present in a pendent group, if present, of the cationic polyaminoacids.

As examples of the cationic polyaminoacids, mention may be made of cationized collagen, cationized gelatin, steardimoium hydroxyprolyl hydrolyzed wheat protein, cocodimonium hydroxypropyl hydrolyzed wheat protein, hydroxypropyltrimonium hydrolyzed conchiolin protein, steardimonium hydroxypropyl hydrolyzed soy protein, hydroxypropyltrimonium hydrolyzed soy protein, cocodimonium hydroxypropyl hydrolyzed soy protein, and the like.

It may be preferable that the cationic polymer be selected from the group consisting of cyclopolymers of alkyldiallylamine and cyclopolymers of dialkyldiallylammonium such as (co)polydiallyldialkyl ammonium chloride, (co) polyamines such as (co)polylysines, cationic (co)polyaminoacids such as cationized collagen, and salts thereof.

The amount of the cationic polymer(s) in the composition according to the present invention may be 0.001% by weight or more, preferably 0.1% by weight or more, and more preferably 1% by weight or more, relative to the total weight of the composition.

The amount of the cationic polymer(s) in the composition according to the present invention may be 25% by weight or less, preferably 20% by weight or less, and more preferably 15% by weight or less, relative to the total weight of the composition.

The amount of the cationic polymer(s) in the composition according to the present invention may be from 0.001 to 25% by weight, preferably from 0.1 to 20% by weight, and more preferably from 1 to 15% by weight, relative to the total weight of the composition.

(Anionic Polymer)

An anionic polymer has a positive charge density. The charge density of the anionic polymer may be from 0.1 meq/g to 20 meq/g, preferably from 1 to 15 meq/g, and more preferably from 4 to 10 meq/g if the anionic polymer is a synthetic anionic polymer, and the average substitution degree of the anionic polymer may be from 0.1 to 3.0, preferably from 0.2 to 2.7, and more preferably from 0.3 to 2.5 if the anionic polymer is a natural anionic polymer.

It may be preferable that the molecular weight of the anionic polymer be 1,000 or more, preferably 10,000 or more, more preferably 50,000 or more, and even more preferably 1,000,00 or more.

The anionic polymer may have at least one negatively chargeable and/or negatively charged moiety selected from the group consisting of a sulfuric group, a sulfate group, a sulfonic group, a sulfonate group, a phosphoric group, a phosphate group, a phosphonic group, a phosphonate group, a carboxylic group, and a carboxylate group.

The anionic polymer may be a homopolymer or a copolymer. The term "copolymer" is understood to mean both copolymers obtained from two kinds of monomers and those obtained from more than two kinds of monomers, such as terpolymers obtained from three kinds of monomers.

The anionic polymer may be selected from natural and synthetic anionic polymers.

The anionic polymer may comprise at least one hydrophobic chain.

The anionic polymer which may comprise at least one hydrophobic chain may be obtained by copolymerization of a monomer (a) chosen from carboxylic acids comprising α,β-ethylenic unsaturation (monomer a') and 2-acrylamido-2-methylpropanesulphonic acid (monomer a") with a non-surface-active monomer (b) comprising an ethylenic unsaturation other than (a) and/or a monomer (c) comprising an ethylenic unsaturation resulting from the reaction of an acrylic monomer comprising an α,β-monoethylenic unsaturation or of an isocyanate monomer comprising a monoethylenic unsaturation with a monohydric nonionic amphiphilic component or with a primary or secondary fatty amine.

Thus, the anionic polymer with at least one hydrophobic chain may be obtained by two synthetic routes:

either by copolymerization of the monomers (a') and (c), or (a'), (b) and (c), or (a") and (c), or (a"), (b) and (c), or by modification (and in particular esterification or amidation) of a copolymer formed from the monomers (a') or from the monomers (a') and (b), or (a") and (b), by a monohydric nonionic amphiphilic compound or a primary or secondary fatty amine.

Mention may in particular be made, as 2-acrylamido-2-methylpropanesulphonic acid copolymers, of those disclosed in the article "Micelle formation of random copolymers of sodium 2-(acrylamido)-2-methylpropanesulfonate and nonionic surfactant macromonomer in water as studied by fluorescence and dynamic light scattering—Macromolecules, 2000, Vol. 33, No. 10-3694-3704" and in applications EP-A-0 750 899 and EP-A-1 069 172.

The carboxylic acid comprising an α,β-monoethylenic unsaturation constituting the monomer (a') can be chosen from numerous acids and in particular from acrylic acid, methacrylic acid, crotonic acid, itaconic acid and maleic acid. It is preferably acrylic or methacrylic acid.

The copolymer can comprise a monomer (b) comprising a monoethylenic unsaturation which does not have a surfactant property. The preferred monomers are those which give water-insoluble polymers when they are homopolymerized. They can be chosen, for example, from $C_1$-$C_4$ alkyl acrylates and methacrylates, such as methyl acrylate, ethyl acrylate, butyl acrylate or the corresponding methacrylates. The more particularly preferred monomers are methyl acrylate and ethyl acrylate. The other monomers which can be used are, for example, styrene, vinyltoluene, vinyl acetate, acrylonitrile and vinylidene chloride. Unreactive monomers are preferred, these monomers being those in which the single ethylenic group is the only group which is reactive under the polymerization conditions. However, monomers which comprise groups which react under the effect of heat, such as hydroxyethyl acrylate, can optionally be used.

The monomer (c) is obtained by reaction of an acrylic monomer comprising α,β-monoethylenic unsaturation, such as (a), or of an isocyanate monomer comprising monoethylenic unsaturation with a monohydric nonionic amphiphilic compound or a primary or secondary fatty amine.

The monohydric nonionic amphiphilic compounds or the primary or secondary fatty amines used to produce the nonionic monomer (c) are well known. The monohydric nonionic amphiphilic compounds are generally alkoxylated hydrophobic compounds comprising an alkylene oxide forming the hydrophilic part of the molecule. The hydrophobic compounds are generally composed of an aliphatic alcohol or an alkylphenol, in which compounds a carbonaceous chain comprising at least six carbon atoms constitutes the hydrophobic part of the amphiphilic compound.

The preferred monohydric nonionic amphiphilic compounds are compounds having the following formula (V):

$$R-(OCH_2CHR')_m-(OCH_2CH_2)_n-OH \quad (V)$$

in which R is chosen from alkyl or alkylene groups comprising from 6 to 30 carbon atoms and alkylaryl groups having alkyl radicals comprising from 8 to 30 carbon atoms, R' is chosen from alkyl groups comprising from 1 to 4 carbon atoms, n is a mean number ranging from approximately 1 to 150 and m is a mean number ranging from approximately 0 to 50, provided that n is at least as great as m.

Preferably, in the compounds of formula (V), the R group is chosen from alkyl groups comprising from 12 to 26 carbon atoms and alkylphenyl groups in which the alkyl group is $C_8$-$C_{13}$; the R' group is the methyl group; m=0 and n=1 to 25.

The preferred primary and secondary fatty amines are composed of one or two alkyl chains comprising from 6 to 30 carbon atoms.

The monomer used to form the nonionic urethane monomer (c) can be chosen from highly varied compounds. Use may be made of any compound comprising a copolymerizable unsaturation, such as an acrylic, methacrylic or allylic unsaturation. The monomer (c) can be obtained in particular from an isocyanate comprising a monoethylenic unsaturation, such as, in particular, α,α-dimethyl-m-isopropenylbenzyl isocyanate.

The monomer (c) can be chosen in particular from acrylates, methacrylates or itaconates of oxyethylenated (1 to 50 EO) $C_6$-$C_{30}$ fatty alcohol, such as steareth-20 methacrylate, oxyethylenated (25 EO) behenyl methacrylate, oxyethylenated (20 EO) monocetyl itaconate, oxyethylenated (20 EO) monostearyl itaconate or the acrylate modified by polyoxyethylenated (25 EO) $C_{12}$-$C_{24}$ alcohols and from dimethyl-m-isopropenylbenzyl isocyanates of oxyethylenated (1 to 50 EO) $C_6$-$C_{30}$ fatty alcohol, such as, in particular, the dimethyl-m-isopropenylbenzyl isocyanate of oxyethylenated behenyl alcohol.

According to a specific embodiment of the present invention, the anionic polymer is chosen from acrylic terpolymers obtained from (a) a carboxylic acid comprising an α,β-ethylenic unsaturation, (b) a non-surface-active monomer comprising an ethylenic unsaturation other than (a), and (c) a nonionic urethane monomer which is the reaction product of a monohydric nonionic amphiphilic compound with an isocyanate comprising a monoethylenic unsaturation.

Mention may in particular be made, as anionic polymers comprising at least one hydrophobic chain, of the acrylic acid/ethyl acrylate/alkyl acrylate terpolymer, such as the product as a 30% aqueous dispersion sold under the name Acusol 823 by Rohm & Haas; the acrylates/steareth-20 methacrylate copolymer, such as the product sold under the name Aculyn 22 by Rohm & Haas; the (meth)acrylic acid/ethyl acrylate/oxyethylenated (25 EO) behenyl methacrylate terpolymer, such as the product as an aqueous emulsion sold under the name Aculyn 28 by Rohm & Haas; the acrylic acid/oxyethylenated (20 EO) monocetyl itaconate copolymer, such as the product as a 30% aqueous dispersion sold under the name Structure 3001 by National Starch; the acrylic acid/oxyethylenated (20 EO) monostearyl itaconate copolymer, such as the product as a 30% aqueous dispersion sold under the name Structure 2001 by National Starch; the acrylates/acrylate modified by polyoxyethylenated (25 EO) $C_{12}$-$C_{24}$ alcohol copolymer, such as the 30-32% copolymer latex sold under the name Synthalen W2000 by 3V SA; or the methacrylic acid/methyl acrylate/dimethyl-meta-isopropenylbenzyl isocyanate of ethoxylated behenyl alcohol terpolymer, such as the product as a 24% aqueous dispersion and comprising 40 ethylene oxide groups disclosed in the document EP-A-0 173 109.

The anionic polymers may also be Polyester-5, such as the product sold under the name of Eastman AQ™ 55S Polymer by EASTMAN CHEMICAL having a chemical formula below.

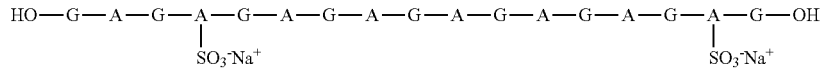

A: dicarboxylic acid moiety
G: glycol moiety
$SO_3^-Na^+$: sodium sulfo group
OH: hydroxyl group It may be preferable that the anionic polymer be selected from the group consisting of polysaccharides such as alginic acid, hyaluronic acid, and cellulose polymers (e.g., carboxymethylcellulose), anionic (co)polyaminoacids such as (co)polyglutamic acids, (co)poly(meth)acrylic acids, (co) polyamic acids, (co)polystyrene sulfonate, (co)poly(vinyl sulfate), dextran sulfate, chondroitin sulfate, (co)polymaleic acids, (co)polyfumaric acids, maleic acid (co)polymers, and salts thereof.

The maleic acid copolymer may comprise one or more maleic acid comonomers, and one or more comonomers chosen from vinyl acetate, vinyl alcohol, vinylpyrrolidone, olefins comprising from 2 to 20 carbon atoms, and styrene.

Thus, the "maleic acid copolymer" is understood to mean any polymer obtained by copolymerization of one or more maleic acid comonomers and of one or more comonomers chosen from vinyl acetate, vinyl alcohol, vinylpyrrolidone, olefins comprising from 2 to 20 carbon atoms, such as octadecene, ethylene, isobutylene, diisobutylene or isooctylene, and styrene, the maleic acid comonomers optionally being partially or completely hydrolysed.

Use will preferably be made of hydrophilic polymers, that is to say polymers having a solubility of water of greater than or equal to 2 g/l.

In an advantageous aspect of the present invention, the maleic acid copolymer may have a molar fraction of maleic acid units of between 0.1 and 1, more preferably between 0.4 and 0.9.

The weight-average molar mass of the maleic acid copolymer may be between 1,000 and 500,000, and preferably between 1,000 and 50,000.

It is preferable that the maleic acid copolymer be a styrene/maleic acid copolymer, and more preferably sodium styrene/maleic acid copolymer.

Use will preferably be made of a copolymer of styrene and of maleic acid in a 50/50 ratio.

Use may be made, for example, of the styrene/maleic acid (50/50) copolymer, in the form of an ammonium salt at 30% in water, sold under the reference SMA1000H® by Cray Valley or the styrene/maleic acid (50/50) copolymer, in the form of a sodium salt at 40% in water, sold under the reference SMA1000HNa® by Cray Valley.

The use of the styrene/maleic acid copolymer such as sodium styrene/maleic acid copolymer can improve the wettability of a film prepared by the composition according to the present invention.

The amount of the anionic polymer(s) in the composition according to the present invention may be 0.001% by weight or more, preferably 0.1% by weight or more, and more preferably 1% by weight or more, relative to the total weight of the composition.

The amount of the anionic polymer(s) in the composition according to the present invention may be 25% by weight or less, preferably 20% by weight or less, and more preferably 15% by weight or less, relative to the total weight of the composition.

The amount of the anionic polymer(s) in the composition according to the present invention may be from 0.001 to 25% by weight, preferably from 0.1 to 20% by weight, and more preferably from 1 to 15% by weight, relative to the total weight of the composition.

(Amphoteric Polymer)

An amphoteric polymer has both a positive charge density and a negative charge density.

The positive charge density of the amphoteric polymer may be from 0.01 meq/g to 20 meq/g, preferably from 0.05 to 15 meq/g, and more preferably from 0.1 to 10 meq/g.

The negative charge density of the amphoteric polymer may be from 0.01 meq/g to 20 meq/g, preferably from 0.05 to 15 meq/g, and more preferably from 0.1 to 10 meq/g.

It may be preferable that the molecular weight of the amphoteric polymer be 500 or more, preferably 1000 or more, more preferably 2000 or more, and even more preferably 5000 or more.

Unless otherwise defined in the descriptions, "molecular weight" means a number average molecular weight.

The amphoteric polymer may have at least one positively chargeable and/or positively charged moiety selected from the group consisting of a primary, secondary or tertiary amino group, a quaternary ammonium group, a guanidine group, a biguanide group, an imidazole group, an imino group, and a pyridyl group, and at least one negatively chargeable and/or negatively charged moiety selected from the group consisting of a sulfuric group, a sulfate group, a sulfonic group, a sulfonate group, a phosphoric group, a phosphate group, a phosphonic group, a phosphonate group, a carboxylic group, and a carboxylate group.

The amphoteric polymer may be a homopolymer or a copolymer. The term "copolymer" is understood to mean both copolymers obtained from two kinds of monomers and those obtained from more than two kinds of monomers, such as terpolymers obtained from three kinds of monomers.

The amphoteric polymers which can be used in accordance with the present invention may be chosen from the polymers containing K and M units distributed randomly in the polymer chain where K denotes a unit which is derived from a monomer containing at least one basic nitrogen atom and M denotes a unit which is derived from an acidic monomer containing one or more carboxylic or sulphonic groups or alternatively K and M may denote groups which are derived from zwitterionic monomers of carboxybetaines or of sulphobetaines. K and M may also denote a cationic polymer chain containing primary, secondary, tertiary or quaternary amine groups, in which at least one of the amine groups carries a carboxylic or sulphonic group linked through a hydrocarbon radical or alternatively K and M form part of a chain of a polymer with an $\alpha,\beta$-dicarboxylic ethylene unit in which one of the carboxylic groups has been caused to react with a polyamine containing one or more primary or secondary amine groups.

The amphoteric polymers corresponding to the definition given above which are more particularly preferred are chosen from the following polymers:

(1) The polymers resulting from the copolymerization of a monomer derived from a vinyl compound carrying a carboxylic group such as more particularly acrylic acid, methacrylic acid, maleic acid, alpha-chloroacrylic acid, and from a basic monomer derived from a substituted vinyl compound containing at least one basic atom such as more particularly dialkylaminoalkyl methacrylate and acrylate, dialkylaminoalkylmethacrylamide and acrylamide. Such compounds are described in U.S. Pat. No. 3,836,537. There may also be mentioned the sodium acrylate/acrylamidopropyltrimethylammonium chloride copolymer sold under the name POLYQUART KE 3033 by the company HENKEL. The vinyl compound may also be a dialkyldiallylammonium salt such as dimethyldiallylammonium chloride. The copolymers of acrylic acid and of the latter monomer are provided under the names MERQUAT 280, MERQUAT 295, MERQUAT 2003 PR, MERQUAT 3330 PR, and MERQUAT PLUS 3330 by the company Lubrizol.

(2) The polymers containing units which are derived from:
a) at least one monomer chosen from acrylamides or methacrylamides substituted on the nitrogen by an alkyl radical,
b) at least one acidic comonomer containing one or more reactive carboxylic groups, and
c) at least one basic comonomer such as esters with primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides most particularly preferred according to the invention are groups whose alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide as well as the corresponding methacrylamides.

The acidic comonomers are chosen more particularly from acrylic, methacrylic, crotonic, itaconic, maleic and fumaric acids as well as the alkyl monoesters having 1 to 4 carbon atoms of maleic or fumaric anhydrides or acids.

The basic comonomers preferred are methacrylates of aminoethyl, butylaminoethyl, N,N'-dimethylaminoethyl, N-tert-butylaminoethyl.

Particularly used are the copolymers whose CTFA name (4th ed. 1991) is Octylacrylamide/acrylates/butylaminoethylmethacrylate copolymer such as the products sold under the name AMPHOMER or LOVOCRYL 47 by the company NATIONAL STARCH.

(3) The partially or completely alkylated and crosslinked polyaminoamides derived from polyaminoamides of the following general formula:

—[—CO—R$_4$—CO—Z—]— in which R$_4$ represents a divalent radical derived from a saturated dicarboxylic acid, a mono- or dicarboxylic aliphatic acid with ethylenic double bond, an ester of a lower alkanol having 1 to 6 carbon atoms of these acids or a radical which is derived from the addition of any one of the said acids with a bis-primary or bis-secondary amine, and Z denotes a radical of a bis-primary, mono- or bis-secondary polyalkylene-polyamine and preferably represents:
a) in the proportions of 60 to 100 mol %, the radical —NH—[(CH$_2$)$_x$—NH—]$_p$— where x=2 and p=2 or 3, or alternatively x=3 and p=2, this radical being derived from the diethylenetriamine, triethylenetetraamine or dipropylenetriamine;
b) in the proportions of 0 to 40 mol %, the radical (IV) above, in which x=2 and p=1 and which is derived from ethylenediamine, or the radical which is derived from piperazine:

c) in the proportions of 0 to 20 mol %, the radical —NH—(CH$_2$)$_6$—NH— which is derived from hexamethylenediamine, these polyamino amines being crosslinked by adding a bifunctional crosslinking agent chosen from the epihalohydrins, diepoxides, dianhydrides, bis-unsaturated derivatives, by means of 0.025 to 0.35 mol of crosslinking agent per amine group of the polyamino amide and alkylated by the action of acrylic acid, chloroacetic acid or of an alkanesultone or of their salts.

The saturated carboxylic acids are preferably chosen from the acids having 6 to 10 carbon atoms such as adipic, 2,2,4-trimethyladipic and 2,4,4-trimethyladipic acid, terephthalic acid, the acids with ethylene double bond such as for example acrylic, methacrylic and itaconic acids.

The alkanesultones used in the alkylation are preferably propane or butanesultone, and the salts of the alkylating agents are preferably the sodium or potassium salts.

(4) The polymers containing zwitterionic units of formula:

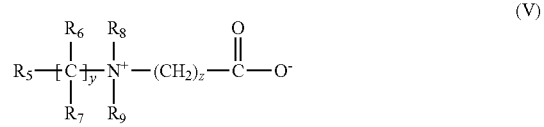

in which R$_5$ denotes a polymerizable unsaturated group such as an acrylate, methacrylate, acrylamide or methacrylamide group, y and z represent an integer from 1 to 3, R$_6$ and R$_7$ represent a hydrogen atom, methyl, ethyl or propyl, R$_8$ and R$_9$ represent a hydrogen atom or an alkyl radical such that the sum of the carbon atoms in R$_8$ and R$_9$ does not exceed 10.

The polymers comprising such units may also comprise units derived from nonzwitterionic monomers such as dimethyl or diethylaminoethyl acrylate or methacrylate or alkyl acrylates or methacrylates, acrylamides or methacrylamides or vinyl acetate.

By way of example, there may be mentioned the copolymer of butyl methacrylate/dimethylcarboxymethylammonioethyl methacrylate such as the product sold under the name DIAFORMER Z301 by the company SANDOZ.

(5) The polymers derived from chitosan containing monomeric units corresponding to the following formulae (VI), (VII), and (VIII):

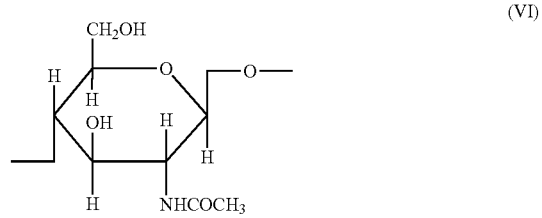

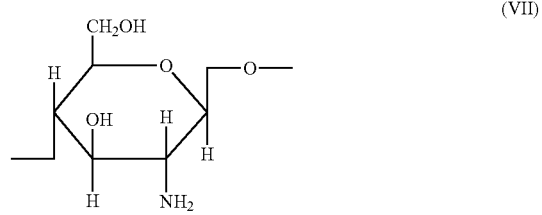

-continued

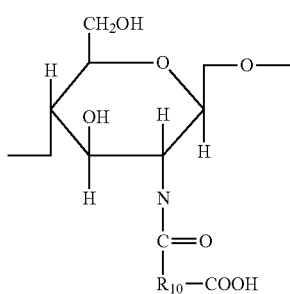
(VIII)

the (VI) unit being present in proportions of from 0 to 30%, the (VII) unit in proportions of from 5 to 50% and the (VIII) unit in proportions of from 30 to 90%, it being understood that in this (VIII) unit, $R_{10}$ represents a radical of formula:

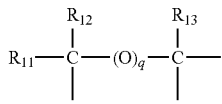

in which if q=0, $R_{11}$, $R_{12}$ and $R_{13}$, which are identical or different, each represent a hydrogen atom, a methyl, hydroxyl, acetoxy or amino residue, a monoalkylamine residue or a dialkylamine residue optionally interrupted by one or more nitrogen atoms and/or optionally substituted with one or more amine, hydroxyl, carboxyl, alkylthio or sulphonic groups, or an alkylthio residue whose alkyl group carries an amino residue, at least one of the $R_{11}$, $R_{12}$ and $R_{13}$ radicals being in this case a hydrogen atom;

or if q=1, $R_{11}$, $R_{12}$ and $R_{13}$ each represent a hydrogen atom, as well as the salts formed by these compounds with bases or acids.

(6) The polymers derived from the N-carboxyalkylation of chitosan such as N-carboxymethyl chitosan or N-carboxybutyl chitosan sold under the name "EVALSAN" by the company JAN DEKKER.

(7) The polymers corresponding to the general formula (IX) such as those described for example in French Patent 1,400,366:

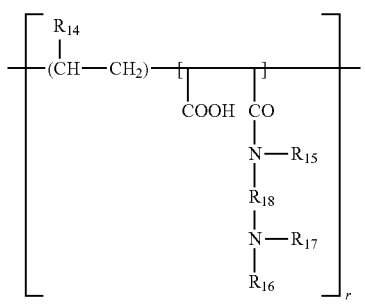
(IX)

in which $R_{14}$ represents a hydrogen atom, a $CH_3O$, $CH_3CH_2O$ or phenyl radical, $R_{15}$ denotes hydrogen or a lower alkyl radical such as methyl or ethyl, $R_{16}$ denotes hydrogen or a lower alkyl radical such as methyl or ethyl, $R_{17}$ denotes a lower alkyl radical such as methyl or ethyl or a radical corresponding to the formula: $—R_{18}—N(R_{16})_2$, $R_{18}$ representing a group $—CH_2—CH_2—$, $—CH_2—CH_2—CH_2—$ or $—CH_2—CH(CH_3)—$, $R_{16}$ having the meanings mentioned above, as well as the higher homologues of these radicals and containing up to 6 carbon atoms.

(8) Amphoteric polymers of the -D-X-D-X— type chosen from:

a) the polymers obtained by the action of chloroacetic acid or sodium chloroacetate on the compounds containing at least one unit of formula:

-D-X-D-X-D- (X)

where D denotes a radical

and X denotes the symbol E or E', E or E', which are identical or different, denote a bivalent radical which is an alkylene radical with a linear or branched chain containing up to 7 carbon atoms in the principal chain which is unsubstituted or substituted with hydroxyl groups and which may contain, in addition, oxygen, nitrogen or sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, or hydroxyl, benzylamine, amine oxide, quaternary ammonium, amide, imide, alcohol, ester and/or urethane groups.

b) The polymers of formula:

-D-X-D-X— (XI)

where D denotes a radical

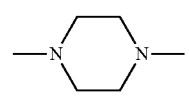

and X denotes the symbol E or E' and, at least once, E'; E having the meaning indicated above and E' is a bivalent radical which is an alkylene radical with a linear or branched chain having up to 7 carbon atoms in the principal chain, which is unsubstituted or substituted with one or more hydroxyl radicals and containing one or more nitrogen atoms, the nitrogen atom being substituted with an alkyl chain optionally interrupted by an oxygen atom and necessarily containing one or more carboxyl functional groups or one or more hydroxyl functional groups and betainized by reaction with chloroacetic acid or sodium chloroacetate.

(9) The copolymers ($C_1$-$C_5$)alkyl vinyl ether/maleic anhydride partially modified by semiamidation with an N,N-dialkylaminoalkylamine such as N,N-dimethylaminopropylamine or by semiesterification with an N,N-dialkanolamine. These copolymers may also contain other vinyl comonomers such as vinylcaprolactam.

The amphoteric polymers particularly preferred according to the invention are those of the family (1), particularly those containing a salt of dialkyldiallyl ammonium as a cationic monomer.

The amphoteric polymers may be chosen from polyquaternium-22, polyquaternium-39, polyquaternium-53, polyquaternium-64, polyquaternium-51, polyquaternium-61 and mixtures thereof. Polyquaternium-39 and polyquaternium-53, for example the product Merquat 3330 PR and Merquat 2003 PR, sold by Lubrizol, are more preferable.

The amount of the amphoteric polymer(s) in the composition according to the present invention may be 0.001% by weight or more, preferably 0.1% by weight or more, and more preferably 1% by weight or more, relative to the total weight of the composition.

The amount of the amphoteric polymer(s) in the composition according to the present invention may be 25% by weight or less, preferably 20% by weight or less, and more preferably 15% by weight or less, relative to the total weight of the composition.

The amount of the amphoteric polymer(s) in the composition according to the present invention may be from 0.001 to 25% by weight, preferably from 0.1 to 20% by weight, and more preferably from 1 to 15% by weight, relative to the total weight of the composition.

[Oil]

The composition according to the present invention comprises (b) at least one oil. If two or more (b) oils are used, they may be the same or different.

Here, "oil" means a fatty compound or substance which is in the form of a liquid or a paste (non-solid) at room temperature (25° C.) under atmospheric pressure (760 mmHg). As the oils, those generally used in cosmetics can be used alone or in combination thereof. These oils may be volatile or non-volatile.

The oil may be a non-polar oil such as a hydrocarbon oil, a silicone oil, or the like; a polar oil such as a plant or animal oil and an ester oil or an ether oil; or a mixture thereof.

The oil may be selected from the group consisting of oils of plant or animal origin, synthetic oils, silicone oils, hydrocarbon oils and fatty alcohols.

As examples of plant oils, mention may be made of, for example, linseed oil, *camellia* oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of animal oils, mention may be made of, for example, squalene and squalane.

As examples of synthetic oils, mention may be made of alkane oils such as isododecane and isohexadecane, ester oils, ether oils, and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the present invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols, and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters, as well as pentaerythrityl tetraethyl hexanoate.

More particularly, use is made of monoesters and diesters and especially sucrose, glucose or methylglucose monooleates or dioleates, stearates, behenates, oleopalmitates, linoleates, linolenates and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrityl tetra(2-ethylhexanoate), 2-ethylhexyl succinate, diethyl sebacate, and mixtures thereof.

As examples of artificial triglycerides, mention may be made of, for example, caproyl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate) and glyceryl tri(caprate/caprylate/linolenate).

As examples of silicone oils, mention may be made of, for example, linear organopolysiloxanes such as dimethylpolysiloxane, methylphenylpolysiloxane, methylhydrogenpolysiloxane, and the like; cyclic organopolysiloxanes such as cyclohexasiloxane, octamethylcyclotetrasiloxane, decamethylcyclopentasiloxane, dodecamethylcyclohexasiloxane, and the like; and mixtures thereof.

Preferably, silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used according to the present invention are silicone oils as defined above and comprise in their structure one or more organofunctional groups attached via a hydrocarbon-based group.

Organopolysiloxanes are defined in greater detail in Walter Noll's *Chemistry and Technology of Silicones* (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, Silbione® 70045 V5 by Rhodia, and dodecamethylcyclopentasiloxane sold under the name Silsoft 1217 by Momentive Performance Materials, and mixtures thereof. Mention may also be made of cyclocopolymers of the type such as dimethylsiloxane/methylalkylsiloxane, such as Silicone Volatile® FZ 3109 sold by the company Union Carbide, of formula:

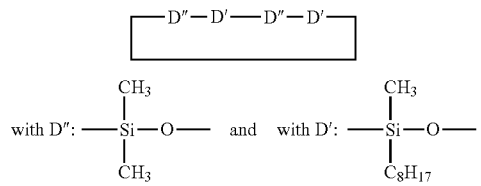

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane; and (ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*. The viscosity of the silicones is measured at 25° C. according to ASTM standard 445 Appendix C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s; and the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

Among the silicones containing aryl groups, mention may be made of polydiarylsiloxanes, especially polydiphenylsiloxanes and polyalkylarylsiloxanes such as phenyl silicone oil.

The phenyl silicone oil may be chosen from the phenyl silicones of the following formula:

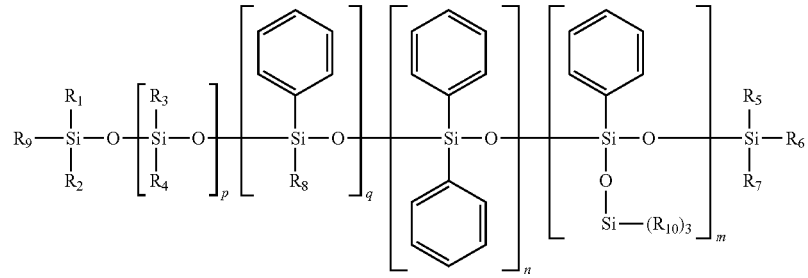

in which $R_1$ to $R_{10}$, independently of each other, are saturated or unsaturated, linear, cyclic or branched $C_1$-$C_{30}$ hydrocarbon-based radicals, preferably $C_1$-$C_{12}$ hydrocarbon-based radicals, and more preferably $C_1$-$C_6$ hydrocarbon-based radicals, in particular methyl, ethyl, propyl or butyl radicals, and m, n, p and q are, independently of each other, integers 0 to 900 inclusive, preferably 0 to 500 inclusive, and more preferably 0 to 100 inclusive, with the proviso that the sum n+m+q is other than 0.

Examples that may be mentioned include the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

certain oils of the SF series from General Electric, such as SF 1023, SF 1154, SF 1250 and SF 1265.

As the phenyl silicone oil, phenyl trimethicone ($R_1$ to $R_{10}$ are methyl; p, q, and n=0; m=1 in the above formula) is preferable.

The organomodified liquid silicones may especially contain polyethyleneoxy and/or polypropyleneoxy groups. Mention may thus be made of the silicone KF-6017 proposed by Shin-Etsu, and the oils Silwet® L722 and L77 from the company Union Carbide.

Hydrocarbon oils may be chosen from:

linear or branched, optionally cyclic, $C_6$-$C_{16}$ lower alkanes. Examples that may be mentioned include hexane, undecane, dodecane, tridecane, and isoparaffins, for instance isohexadecane, isododecane and isodecane; and linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as isohexadecane, isododecane, squalane, mineral oil (e.g., liquid paraffin), paraffin, vaseline or petrolatum, naphthalenes, and the like; hydrogenated polyisobutene, isoeicosan, and decene/butene copolymer; and mixtures thereof.

The term "fatty" in the fatty alcohol means the inclusion of a relatively large number of carbon atoms. Thus, alcohols which have 4 or more, preferably 6 or more, and more preferably 12 or more carbon atoms are encompassed within the scope of fatty alcohols. The fatty alcohol may be saturated or unsaturated. The fatty alcohol may be linear or branched.

The fatty alcohol may have the structure R—OH wherein R is chosen from saturated and unsaturated, linear and branched radicals containing from 4 to 40 carbon atoms, preferably from 6 to 30 carbon atoms, and more preferably from 12 to 20 carbon atoms. In at least one embodiment, R may be chosen from $C_{12}$-$C_{20}$ alkyl and $C_{12}$-$C_{20}$ alkenyl groups. R may or may not be substituted with at least one hydroxyl group.

As examples of the fatty alcohol, mention may be made of lauryl alcohol, cetyl alcohol, stearyl alcohol, isostearyl alcohol, behenyl alcohol, undecylenyl alcohol, myristyl alcohol, octyldodecanol, hexyldecanol, oleyl alcohol, linoleyl alcohol, palmitoleyl alcohol, arachidonyl alcohol, erucyl alcohol, and mixtures thereof.

It is preferable that the fatty alcohol be a saturated fatty alcohol.

Thus, the fatty alcohol may be selected from straight or branched, saturated or unsaturated $C_6$-$C_{30}$ alcohols, preferably straight or branched, saturated $C_6$-$C_{30}$ alcohols, and more preferably straight or branched, saturated $C_{12}$-$C_{20}$ alcohols.

The term "saturated fatty alcohol" here means an alcohol having a long aliphatic saturated carbon chain. It is preferable that the saturated fatty alcohol be selected from any linear or branched, saturated $C_6$-$C_{30}$ fatty alcohols. Among the linear or branched, saturated $C_6$-$C_{30}$ fatty alcohols, linear or branched, saturated $C_{12}$-$C_{20}$ fatty alcohols may preferably be used. Any linear or branched, saturated $C_{16}$-$C_{20}$ fatty alcohols may be more preferably used. Branched $C_{16}$-$C_{20}$ fatty alcohols may be even more preferably used.

As examples of saturated fatty alcohols, mention may be made of lauryl alcohol, cetyl alcohol, stearyl alcohol, isostearyl alcohol, behenyl alcohol, undecylenyl alcohol, myristyl alcohol, octyldodecanol, hexyldecanol, and mixtures thereof. In one embodiment, cetyl alcohol, stearyl alcohol, octyldodecanol, hexyldecanol, or a mixture thereof (e.g., cetearyl alcohol) as well as behenyl alcohol, can be used as a saturated fatty alcohol.

According to at least one embodiment, the fatty alcohol used in the composition according to the present invention is preferably chosen from octyldodecanol, hexyldecanol and mixtures thereof.

It is preferable that the (b) oil be chosen from polar oils, more preferably from ester oils, artificial triglycerides and mixtures thereof, and even more preferably from ester oils, artificial triglycerides and mixtures thereof other than organic lipophilic UV filters, in particular ethylhexyl-methoxycinnamate.

According to the present invention, the (b) oil may be surrounded by a plurality of the (a) particles or the (b) oil may be present in the hollow of a capsule formed by the (a) particles.

In other words, the (b) oil may be covered by the (a) particles, or a capsule formed by the (a) particles includes the (b) oil in the hollow of the capsule.

The (b) oil which is surrounded by the (a) particles or present in the hollow of the capsule formed by the (a) particles cannot directly make contact with a keratin substance such as skin.

Thus, even if the (b) oil has a sticky or greasy feeling of use, the composition according to the present invention may not provide a sticky or greasy feeling of use.

The amount of the (b) oil(s) in the composition according to the present invention may be 0.01% by weight or more, preferably 0.1% by weight or more, and more preferably 1% by weight or more, relative to the total weight of the composition.

The amount of the (b) oil(s) in the composition according to the present invention may be 50% by weight or less, preferably 40% by weight or less, and more preferably 35% by weight or less, relative to the total weight of the composition.

The amount of the (b) oil(s) in the composition according to the present invention may be from 0.01 to 50% by weight, preferably from 0.1 to 40% by weight, and more preferably from 1 to 35% by weight, relative to the total weight of the composition.

[Water]

The composition according to the present invention comprises (c) water.

The amount of the (c) water may be 40% by weight or more, preferably 50% by weight or more, and more preferably 60% by weight or more, relative to the total weight of the composition.

The amount of the (c) water may be 90% by weight or less, preferably 80% by weight or less, and more preferably 70% by weight or less, relative to the total weight of the composition.

The amount of the (c) water may be from 40 to 90% by weight, preferably from 50 to 80% by weight, and more preferably from 60 to 70% by weight, relative to the total weight of the composition.

(Non-Polymeric Acid Having Two or More Acid Dissociation Constants)

The composition according to the present invention may include at least one non-polymeric acid having two or more pKa values or salt(s) thereof, i.e., at least one non-polymeric acid having two or more acid dissociation constants or salt(s) thereof. The pKa value (acid dissociation constant) is well known to those skilled in the art, and should be determined at a constant temperature such as 25° C.

The non-polymeric acid having two or more pKa values or salt(s) thereof can be included in the (a) particle. The non-polymeric acid having two or more pKa values can function as a crosslinker for the cationic polymer, anionic polymer and amphoteric polymers.

The term "non-polymeric" here means that the acid is not obtained by polymerizing two or more monomers. Therefore, the non-polymeric acid does not correspond to an acid obtained by polymerizing two or more monomers such as polycarboxylic acid.

It is preferable that the molecular weight of the non-polymeric acid having two or more pKa values or salt(s) thereof is 1000 or less, preferably 800 or less, and more preferably 700 or less.

There is no limit to the type of the non-polymeric acid having two or more pKa values or salt(s) thereof. Two or more different types of non-polymeric acids having two or more pKa values or salts thereof may be used in combination. Thus, a single type of a non-polymeric acid having two or more pKa values or a salt thereof or a combination of different types of non-polymeric acids having two or more pKa values or salts thereof may be used.

The term "salt" in the present specification means a salt formed by addition of suitable base(s) to the non-polymeric acid having two or more pKa values, which may be obtained from a reaction with the non-polymeric acid having two or more pKa values with the base(s) according to methods known to those skilled in the art. As the salt, mention may be made of metal salts, for example salts with alkaline metal such as Na and K, and salts with alkaline earth metal such as Mg and Ca, and ammonium salts.

The non-polymeric acid having two or more pKa values or salt(s) thereof may be an organic acid or salt(s) thereof, and preferably a hydrophilic or water-soluble organic acid or salt(s) thereof.

The non-polymeric acid having two or more pKa values may have at least two acid groups selected from the group consisting of a carboxylic group, a sulfuric group, a sulfonic group, a phosphoric group, a phosphonic group, a phenolic hydroxyl group, and a mixture thereof.

The non-polymeric acid having two or more pKa values may be a non-polymeric polyvalent acid.

The non-polymeric acid having two or more pKa values may be selected from the group consisting of dicarboxylic acids, disulfonic acids, and diphosphoric acids, and a mixture thereof.

The non-polymeric acid having two or more pKa values or salt(s) thereof may be selected from the group consisting of oxalic acid, malonic acid, succinic acid, glutaric acid, adipic acid, pimelic acid, suberic acid, azelaic acid, sebacic acid, fumaric acid, maleic acid, malic acid, citric acid, aconitic acid, oxaloacetic acid, tartaric acid, and salts thereof; aspartic acid, glutamic acid, and salts thereof; terephthalylidene dicamphor sulfonic acid or salts thereof (Mexoryl SX), Benzophenone-9; phytic acid, and salts thereof; Red 2 (Amaranth), Red 102 (New Coccine), Yellow 5 (Tartrazine), Yellow 6 (Sunset Yellow FCF), Green 3 (Fast Green FCF), Blue 1 (Brilliant Blue FCF), Blue 2 (Indigo Carmine), Red 201 (Lithol Rubine B), Red 202 (Lithol Rubine BCA), Red 204 (Lake Red CBA), Red 206 (Lithol Red CA), Red 207 (Lithol Red BA), Red 208 (Lithol Red SR), Red 219 (Brilliant Lake Red R), Red 220 (Deep Maroon), Red 227 (Fast Acid Magenta), Yellow 203 (Quinoline Yellow WS), Green 201 (Alizanine Cyanine Green F), Green 204 (Pyranine Conc), Green 205 (Light Green SF Yellowish), Blue 203 (Patent Blue CA), Blue 205 (Alfazurine FG), Red 401 (Violamine R), Red 405 (Permanent Re F5R), Red 502 (Ponceau 3R), Red 503 (Ponceau R), Red 504 (Ponceau SX), Green 401 (Naphtol Green B), Green 402 (Guinea Green B), and Black 401 (Naphtol Blue Black); folic acid, ascorbic acid, erythorbic acid, and salts thereof; cystine and salts thereof; EDTA and salts thereof; glycyrrhizin and salts thereof; and a mixture thereof.

It may be preferable that the non-polymeric acid having two or more pKa values or salt(s) thereof be selected from the group consisting of terephthalylidene dicamphor sulfonic acid and salts thereof (Mexoryl SX), Yellow 6 (Sunset Yellow FCF), ascorbic acid, phytic acid and salts thereof, and a mixture thereof.

The amount of the non-polymeric acid having two or more pKa values or salt(s) thereof in the composition according to the present invention may be 0.0001% by weight or more, preferably 0.01% by weight or more, and more preferably 0.1% by weight or more, relative to the total weight of the composition.

The amount of the non-polymeric acid having two or more pKa values or salt(s) thereof in the composition according to the present invention may be 30% by weight or less, preferably 20% by weight or less, and more preferably 15% by weight or less, relative to the total weight of the composition.

The amount of the non-polymeric acid having two or more pKa values or salt(s) thereof in the composition according to the present invention may be from 0.0001 to 30% by weight, preferably from 0.01 to 20% by weight, and more preferably from 0.1 to 15% by weight, relative to the total weight of the composition.

(Non-Polymeric Base Having Two or More Base Dissociation Constants)

The composition according to the present invention may include at least one non-polymeric base having two or more pKb values or salt(s) thereof, i.e., at least one non-polymeric base having two or more base dissociation constants or salt(s) thereof. The pKb value (base dissociation constant) is well known to those skilled in the art, and should be determined at a constant temperature such as 25° C.

The non-polymeric base having two or more pKb values or salt(s) thereof can be included in the (a) particle. The non-polymeric base having two or more pKb values can function as a crosslinker for the cationic polymer, anionic polymer and amphoteric polymers.

The term "non-polymeric" here means that the base is not obtained by polymerizing two or more monomers. Therefore, the non-polymeric base does not correspond to a base obtained by polymerizing two or more monomers such as polyallylamine.

It is preferable that the molecular weight of the non-polymeric base having two or more pKb values or salt(s) thereof be 1000 or less, preferably 800 or less, and more preferably 700 or less.

There is no limit to the type of the non-polymeric base having two or more pKb values or salt(s) thereof. Two or more different types of non-polymeric bases having two or more pKb values or salts thereof may be used in combination. Thus, a single type of a non-polymeric base having two or more pKb values or a salt thereof or a combination of different types of non-polymeric bases having two or more pKb values or salts thereof may be used.

The term "salt" in the present specification means a salt formed by addition of suitable acid(s) to the non-polymeric base having two or more pKb values, which may be obtained from a reaction with the non-polymeric base having two or more pKb values with the acid(s) according to methods known to those skilled in the art. As the salt, mention may be made of ammonium salts, for example salts with inorganic acid such as HCl and $HNO_3$, and salts with organic acid such as carboxylic acids and sulfonic acids.

The non-polymeric base having two or more pKb values or salt(s) thereof may be an organic base or salt(s) thereof, and preferably a hydrophilic or water-soluble organic base or salt(s) thereof.

The non-polymeric base having two or more pKb values may have at least two basic groups selected from the group consisting of an amino group, a guanidine group, a biguanide group, an imidazole group, an imino group, a pyridyl group and a mixture thereof.

The non-polymeric base having two or more pKb values may be selected from the group consisting of non-polymeric diamines such as ethylenediamine, propylenediamine, pentanediamine, hexanediamine, urea and derivatives thereof and guanidine and derivatives thereof, non-polymeric polyamines such as spermine and spermidine, basic amino acids, and a mixture thereof.

The non-polymeric base having two or more pKb values or salt(s) thereof may be selected from the group consisting of arginine, lysine, histidine, cysteine, cystine, tyrosine, tryptophan, ornithine, and a mixture thereof.

It may be preferable that the non-polymeric base having two or more pKb values or salt(s) thereof be selected from the group consisting of arginine, lysine, histidine, and a mixture thereof.

The amount of the non-polymeric base having two or more pKb values or salt(s) thereof in the composition according to the present invention may be 0.0001% by weight or more, preferably 0.01% by weight or more, and more preferably 0.1% by weight or more, relative to the total weight of the composition.

The amount of the non-polymeric base having two or more pKb values or salt(s) thereof in the composition according to the present invention may be 30% by weight or less, preferably 20% by weight or less, and more preferably 15% by weight or less, relative to the total weight of the composition.

The amount of the non-polymeric base having two or more pKb values or salt(s) thereof in the composition according to the present invention may be from 0.0001 to 30% by weight, preferably from 0.01 to 20% by weight, and more preferably from 0.1 to 15% by weight, relative to the total weight of the composition.

[Hydrophobic Amino Acid]

The (a) particle in the composition according to the present invention may include (d) at least one hydrophobic amino acid other than the above non-polymeric acid having two or more pKa values or salt(s) thereof or the above non-polymeric base having two or more pKb values or salt(s) thereof. Two or more hydrophobic amino acids may be used in combination.

The term "hydrophobic amino acid" may be selected from the group consisting of isoleucine, leucine, valine, methionine, phenylalanine, threonine, glycine, cysteine, alanine and mixtures thereof. It is preferable that the (d) hydrophobic amino acid be selected from leucine, phenylalanine and mixtures thereof.

The (d) hydrophobic amino acid may be useful for controlling the hydrophobicity of the (a) particle which may influence the encapsulation ability of the (a) particles, depending on the type of the (b) oil.

The amount of the (d) hydrophobic amino acid(s) in the composition according to the present invention may be 0.001% by weight or more, preferably 0.01% by weight or more, and more preferably 0.1% by weight or more, relative to the total weight of the composition.

The amount of the (d) hydrophobic amino acid(s) in the composition according to the present invention may be 10% by weight or less, preferably 5% by weight or less, and more preferably 1% by weight or less, relative to the total weight of the composition.

The amount of the (d) hydrophobic amino acid(s) in the composition according to the present invention may be from 0.001 to 10% by weight, preferably from 0.01 to 5% by weight, and more preferably from 0.1 to 1% by weight, relative to the total weight of the composition.

[Oil Gelling Agent]

The composition according to the present invention may include (e) at least one oil gelling agent. Two or more oil gelling agents may be used in combination.

The (e) oil gelling agent (lipophilic thickener) can enhance the stability of the composition according to the present invention even if the oil in the composition is less polar or non-polar.

The (e) oil gelling agent may be chosen from gelling agents derived from glutamic acid, gelling agents in polymeric form, and gelling agents in mineral form. The gelling agent includes agents that gel via chemical reticulation and agents that gel via physical reticulation.

N-acyl glutamic acid derivatives may be used as gelling agents derived from glutamic acid. N-acyl glutamic acid derivatives include N-acyl glutamic acid amides and N-acyl glutamic acid esters. In one embodiment, N-acyl glutamic acid amides in which the acyl group represents a $C_8$ to $C_{22}$ alkyl chain are preferred.

Examples of N-acyl glutamic acid derivatives that may be mentioned include N-lauroyl-glutamic acid diethyl amide, N-lauroyl-glutamic acid dibutyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-ethylhexanoyl-L-glutamic acid dibutyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoyl-glutamic acid didecyl amide, N-stearoyl-glutamic acid didodecyl amide, N-stearoyl-glutamic acid ditetradecyl amide, N-stearoyl-glutamic acid dihexadecyl amide, N-stearoyl-glutamic acid distearyl amide and mixtures thereof, and more preferred is N-lauroyl-glutamic acid dibutyl amide, N-stearoyl-glutamic acid dihexyl amide, and mixtures thereof.

The gelling agent is preferably N-acyl glutamic acid dialkylamide, and more preferably N-lauroyl-L-glutamic acid dibutylamide (INCI: dibutyl lauroyl glutamide), manufactured or sold by Ajinomoto under the name GP-1 and N-ethylhexanoyl-L-glutamic acid dibutylamide (INCI: dibutyl ethylhexanoyl glutamide), manufactured or sold by Ajinomoto under the name EB-21.

Lipophilic polyamide polymers may be used as gelling agents in polymeric form. As lipophilic polyamide polymers, mention may be made of polyamides branched with pendent fatty chains and/or terminal fatty chains containing from 12 to 120 carbon atoms and in particular from 12 to 68 carbon atoms, the terminal fatty chains being bonded to the polyamide backbone via ester groups. These polymers are more especially those described in document U.S. Pat. No. 5,783,657 from the company Union Camp. In particular, mention may be made of the polymers of which the INCI name is "ethylenediamine/stearyl dimer dilinoleate copolymer" and "ethylenediamine/stearyl dimer tallate copolymer".

By way of examples of gelling agents, mention may be made of the commercial products sold by the company Bush Boake Allen under the names Uniclear 80, Uniclear 100, Uniclear 80 V, Uniclear 100 V and Uniclear 100 VG. They are sold, respectively, in the form of a gel at 80% (with respect to active material) in a mineral oil and at 100% (with respect to active material).

Modified clays may be used as gelling agents, examples of which include hectorites modified with an ammonium chloride of a $C_{10}$ to $C_{22}$ fatty acid, such as bentonite modified with distearyldimethylammonium chloride, also known as quaternium-18 bentonite, such as the products sold or made under the names Bentone 34 and Bentone 38 VCG by the company Rheox, Claytone XL, Claytone 34 and Claytone 40 sold or made by the company Southern Clay, the modified clays known under the name quaternium-18 benzalkonium bentonites and sold or made under the names Claytone HT, Claytone GR and Claytone PS by the company Southern Clay, the clays modified with stearyldimethylbenzoylammonium chloride, known as stearalkonium bentonites, such as the products sold or made under the names Claytone APA and Claytone AF by the company Southern Clay, and Baragel 24 sold or made by the company Rheox.

The amount of the (e) oil gelling agent(s) in the composition according to the present invention may be 0.001% by weight or more, preferably 0.01% by weight or more, and more preferably 0.1% by weight or more, relative to the total weight of the composition.

The amount of the (e) oil gelling agent(s) in the composition according to the present invention may be 10% by weight or less, preferably 5% by weight or less, and more preferably 1% by weight or less, relative to the total weight of the composition.

The amount of the (e) oil gelling agent(s) in the composition according to the present invention may be from 0.001 to 10% by weight, preferably from 0.01 to 5% by weight, and more preferably from 0.1 to 1% by weight, relative to the total weight of the composition.

[Cosmetic Active Ingredient]

The composition according to the present invention may comprise at least one (additional) cosmetic active ingredient in addition to the (b) oil. There is no limitation to the additional cosmetic active ingredient as long as it is not the (b) oil. Two or more additional cosmetic active ingredients may be used in combination. Thus, a single type of additional cosmetic active ingredient or a combination of different types of additional cosmetic active ingredients may be used.

Among the additional cosmetic active ingredients to be used, mention may be made of hydrophobic or water-insoluble UV filters, anti-oxidants, cleansing agents, free radical scavengers, moisturizers, whitening agents, lipo-regulators, anti-acne agents, antidandruff agents, anti-aging agents, softeners, anti-wrinkle agents, keratolitic agents, fresheners, antibacterial agents, antifungal agents, antiperspirants, deodorants, skin conditioners, anesthetics, nourishing agents, and sebum absorbers or moisture absorbers.

The composition according to the present invention may comprise the additional cosmetic active ingredient(s) in an amount of from 0.01 to 50% by weight, preferably from 0.1 to 40% by weight, more preferably from 1 to 30% by weight, and even more preferably 2 to 20% by weight, relative to the total weight of the composition.

(Hydrophobic or Water-Insoluble UV Filter)

According to a preferred embodiment of the present invention, the additional cosmetic active ingredient may be selected from hydrophobic or water-insoluble UV filters.

There is no limit to the type of the hydrophobic or water-insoluble UV filter. Two or more types of hydrophobic or water-insoluble UV filters may be used in combination. Thus, a single type of hydrophobic or water-insoluble UV filter or a combination of different types of hydrophobic or water-insoluble UV filters may be used. The hydrophobic or water-insoluble UV filter can be selected from the group consisting of an inorganic UV filter, a hydrophobic or water-insoluble organic UV filter, and a mixture thereof.

(Inorganic UV Filter)

The composition according to the present invention may comprise at least one inorganic UV filter. If two or more inorganic UV filters are used, they may be the same or different, preferably the same.

The inorganic UV filter used for the present invention may be active in the UV-A and/or UV-B region. The inorganic UV filter used for the present invention is water-insoluble in solvents such as water and ethanol commonly used in cosmetics, but may be hydrophilic and/or lipophilic.

It is preferable that the inorganic UV filter be in the form of a fine particle such that the mean (primary) particle diameter thereof ranges from 1 nm to 50 nm, preferably 5 nm to 40 nm, and more preferably 10 nm to 30 nm. The mean (primary) particle size or mean (primary) particle diameter here is an arithmetic mean diameter.

The inorganic UV filter can be selected from the group consisting of silicon carbide, metal oxides which may or may not be coated, and mixtures thereof.

Preferably, the inorganic UV filters may be selected from pigments (mean size of the primary particles: generally from 5 nm to 50 nm, preferably from 10 nm to 50 nm) formed of metal oxides, such as, for example, pigments formed of titanium oxide (amorphous or crystalline in the rutile and/or anatase form), iron oxide, zinc oxide, zirconium oxide or cerium oxide, which are all UV photoprotective agents that are well known per se. Preferably, the inorganic UV filters may be selected from titanium oxide, zinc oxide, and more preferably titanium oxide.

The inorganic UV filter may or may not be coated. The inorganic UV filter may have at least one coating. The coating may comprise at least one compound selected from the group consisting of alumina, silica, aluminum hydroxide, silicones, silanes, fatty acids or salts thereof (such as sodium, potassium, zinc, iron, or aluminum salts), fatty alcohols, lecithin, amino acids, polysaccharides, proteins, alkanolamines, waxes such as beeswax, (meth)acrylic polymers, organic UV filters, and (per)fluoro compounds.

It is preferable for the coating to include at least one organic UV filter. As the organic UV filter in the coating, a dibenzoylmethane derivative such as butyl methoxydibenzoylmethane (Avobenzone) and 2,2'-Methylenebis[6-(2H-Benzotriazol-2-yl)-4-(1,1,3,3-Tetramethyl-Butyl)Phenol] (Methylene Bis-Benzotriazolyl Tetramethylbutylphenol) marketed as "TINOSORB M" by BASF may be preferable.

In a known manner, the silicones in the coating(s) may be organosilicon polymers or oligomers comprising a linear or cyclic and branched or cross-linked structure, of variable molecular weight, obtained by polymerization and/or polycondensation of suitable functional silanes and essentially composed of repeated main units in which the silicon atoms are connected to one another via oxygen atoms (siloxane bond), optionally substituted hydrocarbon radicals being connected directly to said silicon atoms via a carbon atom.

The term "silicones" also encompasses silanes necessary for their preparation, in particular alkylsilanes.

The silicones used for the coating(s) can preferably be selected from the group consisting of alkylsilanes, polydialkylsiloxanes, and polyalkylhydrosiloxanes. More preferably still, the silicones are selected from the group consisting of octyltrimethylsilanes, polydimethylsiloxanes, and polymethylhydrosiloxanes.

Of course, the inorganic UV filters made of metal oxides may, before their treatment with silicones, have been treated with other surfacing agents, in particular, with cerium oxide, alumina, silica, aluminum compounds, silicon compounds, or their mixtures.

The coated inorganic UV filter may have been prepared by subjecting the inorganic UV filter to one or more surface treatments of a chemical, electronic, mechanochemical, and/or mechanical nature with any of the compounds as described above, as well as polyethylenes, metal alkoxides (titanium or aluminum alkoxides), metal oxides, sodium hexametaphosphate, and those shown, for example, in Cosmetics & Toiletries, February 1990, Vol. 105, pp. 53-64.

The coated inorganic UV filters may be titanium oxides coated with:
silica, such as the product "Sunveil" from Ikeda;
silica and iron oxide, such as the product "Sunveil F" from Ikeda;
silica and alumina, such as the products "Microtitanium Dioxide MT 500 SA" from Tayca, "Tioveil" from Tioxide, and "Mirasun TiW 60" from Rhodia;
alumina, such as the products "Tipaque TTO-55 (B)" and "Tipaque TTO-55 (A)" from Ishihara, and "UVT 14/4" from Kemira;
alumina and aluminum stearate, such as the product "Microtitanium Dioxide MT 100 T, MT 100 TX, MT 100 Z or MT-01" from Tayca, the products "Solaveil CT-10 W" and "Solaveil CT 100" from Uniqema, and the product "Eusolex T-AVO" from Merck;
alumina and aluminum laurate, such as the product "Microtitanium Dioxide MT 100 S" from Tayca;
iron oxide and iron stearate, such as the product "Microtitanium Dioxide MT 100 F" from Tayca;
zinc oxide and zinc stearate, such as the product "BR351" from Tayca;
silica and alumina and treated with a silicone, such as the products "Microtitanium Dioxide MT 600 SAS", "Microtitanium Dioxide MT 500 SAS", and "Microtitanium Dioxide MT 100 SAS" from Tayca;
silica, alumina, and aluminum stearate and treated with a silicone, such as the product "STT-30-DS" from Titan Kogyo;
silica and treated with a silicone, such as the product "UV-Titan X 195" from Kemira; alumina and treated with a silicone, such as the products "Tipaque TTO-55 (S)" from Ishihara or "UV Titan M 262" from Kemira;
triethanolamine, such as the product "STT-65-S" from Titan Kogyo;
stearic acid, such as the product "Tipaque TTO-55 (C)" from Ishihara; or
sodium hexametaphosphate, such as the product "Microtitanium Dioxide MT 150 W" from Tayca.

Other titanium oxide pigments treated with a silicone are preferably $TiO_2$ treated with octyltrimethylsilane and for which the mean size of the individual particles is from 25 and 40 nm, such as that marketed under the trademark "T 805" by Degussa Silices, $TiO_2$ treated with a polydimethylsiloxane and for which the mean size of the individual particles is 21 nm, such as that marketed under the trademark "70250 Cardre UF $TiO_2Si_3$" by Cardre, and anatase/rutile $TiO_2$ treated with a polydimethylhydrosiloxane and for which the mean size of the individual particles is 25 nm, such as that marketed under the trademark "Microtitanium Dioxide USP Grade Hydrophobic" by Color Techniques.

Preferably, the following coated $TiO_2$ can be used as the coated inorganic UV filter: Stearic acid (and) Aluminum Hydroxide (and) $TiO_2$, such as the product "MT-100 TV" from Tayca, with a mean primary particle diameter of 15 nm;
Dimethicone (and) Stearic Acid (and) Aluminum Hydroxide (and) $TiO_2$, such as the product "SA-TTO-S4" from Miyoshi Kasei, with a mean primary particle diameter of 15 nm; Silica (and) $TiO_2$, such as the product "MT-100 WP" from Tayca, with a mean primary particle diameter of 15 nm;
Dimethicone (and) Silica (and) Aluminum Hydroxide (and) $TiO_2$, such as the product "MT-Y02" and "MT-Y-110 M3 S" from Tayca, with a mean primary particle diameter of 10 nm; Dimethicone (and) Aluminum Hydroxide (and) $TiO_2$, such as the product "SA-TTO-S3" from Miyoshi Kasei, with a mean primary particle diameter of 15 nm;
Dimethicone (and) Alumina (and) $TiO_2$, such as the product "UV TITAN M170" from Sachtleben, with a mean primary particle diameter of 15 nm; and
Silica (and) Aluminum Hydroxide (and) Alginic Acid (and) $TiO_2$, such as the product "MT-100 AQ" from Tayca, with a mean primary particle diameter of 15 nm.

In terms of UV filtering ability, $TiO_2$ coated with at least one organic UV filter is more preferable. For example, Avobenzone (and) Stearic Acid (and) Aluminum Hydroxide (and) $TiO_2$, such as the product "HXMT-100ZA" from Tayca, with a mean primary particle diameter of 15 nm, can be used.

The uncoated titanium oxide pigments are, for example, marketed by Tayca under the trademarks "Microtitanium Dioxide MT500B" or "Microtitanium Dioxide MT600B", by Degussa under the trademark "P 25", by Wacker under the trademark "Oxyde de titane transparent PW", by Miyoshi Kasei under the trademark "UFTR", by Tomen under the trademark "ITS", and by Tioxide under the trademark "Tioveil AQ".

The uncoated zinc oxide pigments are, for example:
those marketed under the trademark "Z-cote" by Sunsmart;
those marketed under the trademark "Nanox" by Elementis; and those marketed under the trademark "Nanogard WCD 2025" by Nanophase Technologies.

The coated zinc oxide pigments are, for example:
those marketed under the trademark "Oxide Zinc CS-5" by Toshiba (ZnO coated with polymethylhydrosiloxane);
those marketed under the trademark "Nanogard Zinc Oxide FN" by Nanophase Technologies (as a 40% dispersion in Finsolv TN, $C_{12}$-$C_{15}$ alkyl benzoate);
those marketed under the trademark "Daitopersion Zn-30" and "Daitopersion Zn-50" by Daito (dispersions in oxyethylenated polydimethylsiloxane/cyclopolymethylsiloxane comprising 30% or 50% of zinc nano-oxides coated with silica and polymethylhydrosiloxane); those marketed under the trademark "NFD Ultrafine ZnO" by Daikin (ZnO coated with phosphate of perfluoroalkyl and a copolymer based on perfluoroalkylethyl as a dispersion in cyclopentasiloxane);
those marketed under the trademark "SPD-Z1" by Shin-Etsu (ZnO coated with a silicone-grafted acrylic polymer dispersed in cyclodimethylsiloxane);
those marketed under the trademark "Escalol Z100" by ISP (alumina-treated ZnO dispersed in an ethylhexyl methoxycinnamate/PVP-hexadecene copolymer/methicone mixture);
those marketed under the trademark "Fuji ZnO-SMS-10" by Fuji Pigment (ZnO coated with silica and polymethylsilsesquioxane); and those marketed under the trademark "Nanox Gel TN" by Elementis (ZnO dispersed at 55% in $C_{12}$-$C_{15}$ alkyl benzoate with hydroxystearic acid polycondensate).

The uncoated cerium oxide pigments are marketed, for example, under the trademark "Colloidal Cerium Oxide" by Rhone-Poulenc.

The uncoated iron oxide pigments are, for example, marketed by Amaud under the trademarks "Nanogard WCD 2002 (FE 45B)", "Nanogard Iron FE 45 BL AQ", "Nanogard FE 45R AQ", and "Nanogard WCD 2006 (FE 45R)", or by Mitsubishi under the trademark "TY-220".

The coated iron oxide pigments are, for example, marketed by Arnaud under the trademarks "Nanogard WCD 2008 (FE 45B FN)", "Nanogard WCD 2009 (FE 45B 556)", "Nanogard FE 45 BL 345", and "Nanogard FE 45 BL", or by BASF under the trademark "Oxyde de fer transparent".

Mention may also be made of mixtures of metal oxides, in particular, of titanium dioxide and of cerium dioxide, including a mixture of equal weights of titanium dioxide coated with silica and of cerium dioxide coated with silica marketed by Ikeda under the trademark "Sunveil A", and also a mixture of titanium dioxide and of zinc dioxide coated with alumina, with silica and with silicone, such as the product "M 261" marketed by Kemira, or coated with alumina, with silica, and with glycerol, such as the product "M 211" marketed by Kemira.

Coated inorganic UV filters are preferable, because the UV filtering effects of the inorganic UV filters can be enhanced. In addition, the coating(s) may help uniformly or homogeneously disperse the UV filters in the composition according to the present invention.

If inorganic UV filter(s) in the form of fine particles is/are used, a film according to the present invention which can be prepared from the composition according to the present invention may also have an effect of not providing a white appearance but a transparent or clear appearance, because the fine particles of the inorganic UV filters do not aggregate but can be spread uniformly or homogeneously in the film. It should be noted that free fine particles of inorganic UV filter(s) easily aggregate to give a white appearance to the skin.

(Hydrophobic or Water-Insoluble Organic UV Filter)

The composition according to the present invention may comprise at least one hydrophobic or water-insoluble organic UV filter. If two or more hydrophobic or water-insoluble organic UV filters are used, they may be the same or different, preferably the same.

The hydrophobic or water-insoluble organic UV filter used for the present invention may be active in the UV-A and/or UV-B region. The hydrophobic or water-insoluble organic UV filter may be lipophilic.

The hydrophobic or water-insoluble organic UV filter may be solid or liquid. The terms "solid" and "liquid" mean solid and liquid, respectively, at 25° C. under 1 atm.

The hydrophobic or water-insoluble organic UV filter can be selected from the group consisting of anthranilic compounds; dibenzoylmethane compounds; cinnamic compounds; salicylic compounds; camphor compounds; benzophenone compounds; β,β-diphenylacrylate compounds; triazine compounds; benzotriazole compounds; benzalmalonate compounds; benzimidazole compounds; imidazoline compounds; bis-benzoazolyl compounds; p-aminobenzoic acid (PABA) compounds; methylenebis(hydroxyphenylbenzotriazole) compounds; benzoxazole compounds; screening polymers and screening silicones; dimers derived from α-alkylstyrene; 4,4-diarylbutadiene compounds; guaiazulene and derivatives thereof; rutin and derivatives thereof; and mixtures thereof.

Mention may be made, as examples of the hydrophobic or water-insoluble organic UV filter(s), of those denoted below under their INCI names, and mixtures thereof.

Anthranilic compounds: Menthyl anthranilate, marketed under the trademark "Neo Heliopan MA" by Haarmann and Reimer.

Dibenzoylmethane compounds: Butyl methoxydibenzoylmethane, marketed in particular under the trademark "Parsol 1789" by Hoffmann-La Roche; and isopropyl dibenzoylmethane.

Cinnamic compounds: Ethylhexyl methoxycinnamate, marketed in particular under the trademark "Parsol MCX" by Hoffmann-La Roche; isopropyl methoxycinnamate; isopropoxy methoxycinnamate; isoamyl methoxycinnamate, marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate.

Salicylic compounds: Homosalate (homomentyl salicylate), marketed under the trademark "Eusolex HMS" by Rona/EM Industries; ethylhexyl salicylate, marketed under the trademark "Neo Heliopan OS" by Haarmann and Reimer; glycol salicylate; butyloctyl salicylate; phenyl salicylate; dipropyleneglycol salicylate, marketed under the trademark "Dipsal" by Scher; and TEA salicylate, marketed under the trademark "Neo Heliopan TS" by Haarmann and Reimer.

Camphor compounds, in particular, benzylidenecamphor derivatives: 3-benzylidene camphor, manufactured under the trademark "Mexoryl SD" by Chimex; 4-methylbenzylidene camphor, marketed under the trademark "Eusolex 6300" by Merck; benzylidene camphor sulfonic acid, manufactured under the trademark "Mexoryl SL" by Chimex; camphor benzalkonium methosulfate, manufactured under the trademark "Mexoryl SO" by Chimex; and polyacrylamidomethyl benzylidene camphor, manufactured under the trademark "Mexoryl SW" by Chimex.

Benzophenone compounds: Benzophenone-1 (2,4-dihydroxybenzophenone), marketed under the trademark "Uvinul 400" by BASF; benzophenone-2 (Tetrahydroxybenzophenone), marketed under the trademark "Uvinul D50" by BASF; Benzophenone-3 (2-hydroxy-4-methoxybenzophenone) or oxybenzone, marketed under the trademark "Uvinul M40" by BASF; benzophenone-4 (hydroxymethoxy benzophonene sulfonic acid), marketed under the trademark "Uvinul MS40" by BASF; benzophenone-5 (Sodium hydroxymethoxy benzophenone Sulfonate); benzophenone-6 (dihydroxy dimethoxy benzophenone); marketed under the trademark "Helisorb 11" by Norquay; benzophenone-8, marketed under the trademark "Spectra-Sorb UV-24" by American Cyanamid; benzophenone-9 (Disodium dihydroxy dimethoxy benzophenonedisulfonate), marketed under the trademark "Uvinul DS-49" by BASF; benzophenone-12, and n-hexyl 2-(4-diethylamino-2-hydroxybenzoyl)benzoate (UVINUL A+ by BASF).

β,β-Diphenylacrylate compounds: Octocrylene, marketed in particular under the trademark "Uvinul N539" by BASF; and Etocrylene, marketed in particular under the trademark "Uvinul N35" by BASF.

Triazine compounds: Diethylhexyl butamido triazone, marketed under the trademark "Uvasorb HEB" by Sigma 3V; 2,4,6-tris(dineopentyl 4'-aminobenzalmalonate)-s-triazine, bis-ethylhexyloxyphenol methoxyphenyl triazine marketed under the trademark «TINOSORB S» by CIBA GEIGY, and ethylhexyl triazone marketed under the trademark «UVINUL T150 » by BASF.

Benzotriazole compounds, in particular, phenylbenzotriazole derivatives: 2-(2H-benzotriazole-2-yl)-6-dodecyl-4-methylpheno, branched and linear; and those described in U.S. Pat. No. 5,240,975.

Benzalmalonate compounds: Dineopentyl 4'-methoxybenzalmalonate, and polyorganosiloxane comprising benzalmalonate functional groups, such as polysilicone-15, marketed under the trademark "Parsol SLX" by Hoffmann-LaRoche.

Benzimidazole compounds, in particular, phenylbenzimidazole derivatives.

Imidazoline compounds: Ethylhexyl dimethoxybenzylidene dioxoimidazoline propionate.

Bis-benzoazolyl compounds: The derivatives as described in EP-669,323 and U.S. Pat. No. 2,463,264.

Para-aminobenzoic acid compounds: PABA (p-aminobenzoic acid), ethyl PABA, Ethyl dihydroxypropyl PABA, pentyl dimethyl PABA, ethylhexyl dimethyl PABA, marketed in particular under the trademark "Escalol 507" by ISP, glyceryl PABA, and PEG-25 PABA, marketed under the trademark "Uvinul P25" by BASF.

Methylene bis-(hydroxyphenylbenzotriazol) compounds, such as 2,2'-methylenebis[6-(2H-benzotriazol-2-yl)-4-methyl-phenol] marketed in the solid form under the trademark "Mixxim BB/200" by Fairmount Chemical, 2,2'-methylenebis[6-(2H-benzotriazol-2-yl)-4-(1,1,3,3-tetramethylbutyl)phenol] marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071, 5,166,355, GB-2,303,549, DE-197,26,184 and EP-893,119, and Drometrizole trisiloxane, marketed under the trademark "Silatrizole" by Rhodia Chimie or "Mexoryl XL" by L'Oreal, as represented below.

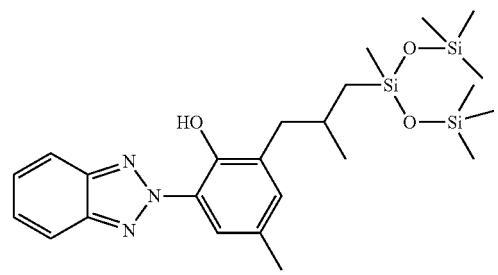 [SMILES: Cc1cc(CC(C)C[Si](C)(O[Si](C)(C)C)O[Si](C)(C)C)c(O)c(-n2nc3ccccc3n2)c1]

Benzoxazole compounds: 2,4-bis[5-1 (dimethylpropyl) benzoxazol-2-yl-(4-phenyl)imino]-6-(2-ethylhexyl) imino-1,3,5-triazine, marketed under the trademark of Uvasorb K2A by Sigma 3V.

Screening polymers and screening silicones: The silicones described in WO 93/04665.

Dimers derived from α-alkylstyrene: The dimers described in DE-19855649.

4,4-Diarylbutadiene compounds: 1,1-dicarboxy(2,2'-dimethylpropyl)-4,4-diphenylbutadiene.

It is preferable that the hydrophobic or water-insoluble organic UV filter(s) be selected from the group consisting of: butyl methoxydibenzoylmethane, ethylhexyl methoxycinnamate, homosalate, ethylhexyl salicylate, octocrylene, benzophenone-3, benzophenone-4, benzophenone-5, n-hexyl 2-(4-diethylamino-2-hydroxybenzoyl) benzoate, 1,1'-(1,4-piperazinediyl)bis[1-[2-[4-(diethylamino)-2-hydroxybenzoyl]phenyl]-methanone 4-methylbenzylidene camphor, ethylhexyl triazone, bis-ethylhexyloxyphenol methoxyphenyl triazine, diethylhexyl butamido triazone, 2,4,6-tris(dineopentyl 4'-aminobenzalmalonate)-s-triazine, 2,4,6-tris(diisobutyl 4'-aminobenzalmalonate)-s-triazine, 2,4-bis-(n-butyl 4'-aminobenzalmalonate)-6-[(3-{1,3,3,3-tetramethyl-1-[(trimethylsilyloxy]disiloxanyl}propyl) amino]-s-triazine, 2,4,6-tris-(di-phenyl)-triazine, 2,4,6-tris-(ter-phenyl)-triazine, methylene bis-benzotriazolyl tetramethylbutylphenol, drometrizole trisiloxane, polysilicone-15, dineopentyl 4'-methoxybenzalmalonate, 1,1-dicarboxy(2,2'-dimethylpropyl)-4,4-diphenylbutadiene, 2,4-bis[5-1 (dimethylpropyl)benzoxazol-2-yl-(4-phenyl)imino]-6-(2-ethylhexyl)imino-1,3,5-triazine, camphor benzylkonium methosulfate and mixtures thereof.

(Whitening Agent)

According to a preferred embodiment of the present invention, the cosmetic active ingredient may be selected from whitening agents.

There is no limit to the type of whitening agent. Two or more types of whitening agents may be used in combination. Thus, a single type of whitening agent or a combination of different types of whitening agents may be used.

As examples of the whitening agent, mention may be made of ascorbic acid or derivatives thereof, kojic acid or derivatives thereof, tranexamic acid or derivatives thereof, resorcinol or derivatives thereof, alkoxysalicylic acid or salts thereof, adenosine phosphate or salts thereof, hydroquinone or glycosides thereof or derivatives thereof, glutathione, 4-(4-hydroxyphenyl)-2-butanol, magnolignan (5,5'-dipropyl-biphenyl-2,2'-diol), chamomilla recutita, and the like.

Ascorbic acid has a D-configuration or L-configuration, and the L-configuration one is preferably employed. Ascorbic acid is also referred to as vitamin C, and has effects of inhibiting the production of melanin due to the strong reduction effects of ascorbic acid. The derivatives of ascorbic acid may be salts of ascorbic acid, and the salts of ascorbic acid are preferably selected from sodium ascorbate, magnesium ascorbyl phosphate, and sodium ascorbyl phosphate. The derivatives of ascorbic acids may be glycosides of ascorbic acid or esters of ascorbic acid. As an example of glycosides of ascorbic acid, mention may be made of, for example, ascorbyl glucoside. As examples of esters of ascorbic acid, mention may be made of, for example, silyl ascorbate, tocopheryl ascorbate, and alkyl ascorbate. As the alkyl ascorbate, methyl ascorbate or ethyl ascorbate is preferably used. In particular, ascorbyl glucoside is preferable. Ascorbic acid or derivatives thereof can be used alone or in combination with two or more types thereof.

As detailed examples of derivatives of ascorbic acid, mention may be made of, for example, 5,6-di-O-dimethylsilyl ascorbate, which is commercially available as PRO-AA from Exsymol SAM; dl-alpha-tocopheryl-2-1-ascorbyl phosphate which is commercially available as SEPIVITAL EPC from Senju Pharmaceutical Co., Ltd.; sodium ascorbyl phosphate which is commercially available as Stay-C 50 from Roche; ascorbyl glucoside which is commercially available from Hayashibara Biochemical Labs., Inc.; 3-O-ethyl ascorbic acid; and the like.

Ascorbic acid or the derivative thereof is preferably used in combination with a copolymer of styrene and maleic anhydride. In particular, at least one part of the maleic anhydride unit of the aforementioned copolymer is preferably hydrolyzed. The aforementioned hydrolyzed maleic anhydride unit may be in the form of an alkaline salt such as a sodium salt, a potassium salt, a lithium salt, or the like. The aforementioned maleic anhydride unit preferably occupies 0.4 to 0.9 mol per one mol of the entire copolymer, and a ratio of the maleic anhydride unit and the styrene unit is preferably 50:50. In particular, it is preferable that the ratio of the maleic anhydride unit and the styrene unit be preferably 50:50, and the ammonium salt or sodium salt be used. By employing ascorbic acid or the derivative thereof in combination with the aforementioned copolymer, stability of ascorbic acid or the derivative thereof is improved. As the aforementioned copolymer, for example, a copolymer of styrene and maleic anhydride (50/50) in the form of an ammonium salt in a concentration of 30% in water, which is commercially available as product number SMA 1000 H (trademark) from Atofina Chemicals Inc.; or a copolymer of styrene and maleic anhydride (50/50) in the form of a sodium salt in a concentration of 40% in water, which is commercially available as product number SMA 1000 H Na (trademark) from Atofina Chemicals Inc., can be used. The aforementioned copolymer is used in a concentration ranging from 0.1 to 20% by weight, and preferably ranging from 0.1 to 10% by weight, with respect to the total weight of the whitening agent for topical application.

As an example of derivatives of kojic acid, mention may be made of, for example, kojic acid glucoside.

As examples of derivatives of tranexamic acid, mention may be made of dimers of tranexamic acid (such as hydrochloric acid trans-4-(trans-aminomethylcyclohexanecarbonyl)aminomethylcyclohexane carboxylic acid), esters of tranexamic acid and hydroquinone (such as 4'-hydroxyphenyl trans-4-aminomethylcyclohexane carboxylate), esters of tranexamic acid and gentisic acid (such as 2-(trans-4-aminomethylcyclohexanecarbonyloxy)-5-hydroxybenzoic acid and salts thereof), tranexamic amides (such as trans-4-aminomethylcyclohexanecarboxylic acid methylamide and salts thereof, trans-4-(p-methoxybenzoyl)aminomethylcyclohexane carboxylic acid and salts thereof, and trans-4-guanidinomethylcyclohexane carboxylic acid and salts thereof), and the like.

As examples of derivatives of resorcinol, mention may be made of, for example, 4-n-butylresorcinol (Rucinol) and the like.

An alkoxysalicylic acid is a compound in which any one of the hydrogen atoms in the 3-position, the 4-position, or the 5-position of salicylic acid is substituted by an alkoxy group. The aforementioned alkoxy group is preferably any one of a methoxy group, an ethoxy group, a propoxy group, an isopropoxy group, a butoxy group, and an isobutoxy group, and is more preferably a methoxy group or an ethoxy group. As examples of the compound, mention may be made of, for example, 3-methoxysalicylic acid, 3-ethoxysalicylic acid, 4-methoxysalicylic acid, 4-ethoxysalicylic acid, 4-propoxysalicylic acid, 4-isopropoxysalicylic acid, 4-butoxysalicylic acid, 5-methoxysalicylic acid, 5-ethoxysalicylic acid, 5-propoxysalicylic acid, and the like. Salts of the alkoxysalicylic acids are not particularly limited. As examples thereof, mention may be made of, for example, alkali metal salts or alkaline earth metal salts such as sodium salts, potassium salts, calcium salts, and the like, ammonium salts, amino acid salts, and the like. A potassium salt of 4-methoxysalicylic acid is preferable.

As examples of adenosine phosphate or salts thereof, mention may be made of, for example, disodium adenosine phosphate, and the like.

As examples of glycosides of hydroquinone, mention may be made of, for example, hexose glycosides such as hydroquinone alpha-D-glucose, hydroquinone beta-D-glucose, hydroquinone alpha-L-glucose, hydroquinone beta-L-glucose, hydroquinone alpha-D-galactose, hydroquinone beta-D-galactose, hydroquinone alpha-L-galactose, hydroquinone beta-L-galactose, and the like; pentose glycosides such as hydroquinone alpha-D-ribose, hydroquinone beta-D-ribose, hydroquinone alpha-L-ribose, hydroquinone beta-L-ribose, hydroquinone alpha-D-arabinose, hydroquinone beta-D-arabinose, hydroquinone alpha-L-arabinose, hydroquinone beta-L-arabinose, and the like; aminosugar glycosides such as hydroquinone alpha-D-glucosamine, hydroquinone beta-D-glucosamine, hydroquinone alpha-L-glucosamine, hydroquinone beta-L-glucosamine, hydroquinone alpha-D-galactosamine, hydroquinone beta-D-galactosamine, hydroquinone alpha-L-galactosamine, hydroquinone beta-L-galactosamine, and the like; urocanic acid glycosides such as hydroquinone alpha-D-glucuronic acid, hydroquinone beta-D-glucuronic acid, hydroquinone alpha-L-glucuronic acid, hydroquinone beta-L-glucuronic acid, hydroquinone alpha-D-galacturonic acid, hydroquinone beta-D-galacturonic acid, hydroquinone alpha-L-galacturonic acid, hydroquinone beta-L-galacturonic acid, and the like; and the like. Among these compounds, hydroquinone beta-D-glucose (hereinafter, referred to as "arbutin") is preferable. As examples of derivatives of hydroquinone or glycosides thereof, mention may be made of, for example, salts of hydroquinone or glycosides thereof. In particular, as examples of arbutin derivatives, mention may be made of, for example, 6-O-caffeoylarbutin, and the like.

As the whitening active ingredients, in particular, L-ascorbic acid or derivatives thereof, kojic acid or derivatives thereof, tranexamic acid or derivatives thereof, arbutin or derivatives thereof, and Rucinol are preferable, and ascorbic acid derivatives such as 3-O-ethyl L-ascorbic acid and L-ascorbic acid glucoside are more preferable.

[pH]

The pH of the composition according to the present invention may be from 3 to 9, preferably from 3.5 to 8.5, and more preferably from 4 to 8.

At a pH of from 3 to 9, the (a) particle can be very stable.

The pH of the composition according to the present invention may be adjusted by adding at least one alkaline agent and/or at least one acid other than the (d) acid to be incorporated into the (a) particle. The pH of the composition according to the present invention may also be adjusted by adding at least one buffering agent.

(Alkaline Agent)

The composition according to the present invention may comprise at least one alkaline agent. Two or more alkaline agents may be used in combination. Thus, a single type of alkaline agent or a combination of different types of alkaline agents may be used.

The alkaline agent may be an inorganic alkaline agent. It is preferable that the inorganic alkaline agent be selected from the group consisting of ammonia; alkaline metal hydroxides; alkaline earth metal hydroxides; alkaline metal phosphates and monohydrogenophosphates such as sodium phosphate or sodium monohydrogen phosphate.

As examples of the inorganic alkaline metal hydroxides, mention may be made of sodium hydroxide and potassium hydroxide. As examples of the alkaline earth metal hydroxides, mention may be made of calcium hydroxide and magnesium hydroxide. As an inorganic alkaline agent, sodium hydroxide is preferable.

The alkaline agent may be an organic alkaline agent. It is preferable that the organic alkaline agent be selected from the group consisting of monoamines and derivatives thereof; diamines and derivatives thereof; polyamines and derivatives thereof; basic amino acids and derivatives thereof; oligomers of basic amino acids and derivatives thereof; polymers of basic amino acids and derivatives thereof; urea and derivatives thereof; and guanidine and derivatives thereof.

As examples of the organic alkaline agents, mention may be made of alkanolamines such as mono-, di- and tri-ethanolamine, and isopropanolamine; urea, guanidine and their derivatives; basic amino acids such as lysine, ornithine or arginine; and diamines such as those described in the structure below:

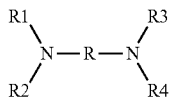

wherein R denotes an alkylene such as propylene optionally substituted by a hydroxyl or a $C_1$-$C_4$ alkyl radical, and $R_1$, $R_2$, $R_3$ and $R_4$ independently denote a hydrogen atom, an alkyl radical or a $C_1$-$C_4$ hydroxyalkyl radical, which may be exemplified by 1,3-propanediamine and derivatives thereof. Arginine, urea and monoethanolamine are preferable.

The alkaline agent(s) may be used in a total amount of from 0.1 to 20% by weight, preferably from 0.2 to 10% by weight, more preferably from 0.3 to 5% by weight, relative to the total weight of the composition, depending on their solubility.

(Acid)

The composition according to the present invention may comprise at least one acid other than the (d) acid to be incorporated into the (a) particle. Two or more acids may be used in combination. Thus, a single type of acid or a combination of different types of acids may be used.

As the acid, mention may be made of any inorganic or organic acids, preferably inorganic acids, which are commonly used in cosmetic products. A monovalent acid and/or a polyvalent acid may be used. A monovalent acid such as citric acid, lactic acid, sulfuric acid, phosphoric acid and hydrochloric acid (HCl) may be used. HCl is preferable.

The acid(s) may be used in a total amount of from 0.1 to 15% by weight, preferably from 0.2 to 10% by weight, more preferably from 0.3 to 5% by weight, relative to the total weight of the composition, depending on their solubility.

(Buffering Agent)

The composition according to the present invention may comprise at least one buffering agent. Two or more buffering agents may be used in combination. Thus, a single type of buffering agent or a combination of different types of buffering agents may be used.

As the buffering agent, mention may be made of an acetate buffer (for example, acetic acid+sodium acetate), a phosphate buffer (for example, sodium dihydrogen phosphate+di-sodium hydorogen phosphate), a citrate buffer (for example, citric acid+sodium citrate), a borate buffer (for example, boric acid+sodium borate), a tartrate buffer (for example, tartaric acid+sodium tartrate dihydrate), Tris buffer (for example, tris(hydroxymethyl)aminomethane), Hepes buffer (4-(2-hydroxyethyl)-1-piperazineethanesulfonic acid).

[Optional Additives]

The composition according to the present invention may comprise, in addition to the aforementioned components, components typically employed in cosmetics, specifically, surfactants or emulsifiers, hydrophilic thickeners, organic non-volatile solvents, silicones and silicone derivatives other than the (b) oil, natural extracts derived from animals or vegetables, waxes, and the like, within a range which does not impair the effects of the present invention.

The composition according to the invention may also comprise at least one fatty acid. The fatty acid may be useful for controlling the hydrophobicity of the (a) particles which may influence the encapsulation ability of the (a) particles, depending on the type of the (b) oil.

The composition according to the present invention may comprise the above optional additive(s) in an amount of from 0.01 to 50% by weight, preferably from 0.05 to 30% by weight, and more preferably from 0.1 to 10% by weight, relative to the total weight of the composition.

However, it is preferable that the composition according to the present invention include a very limited amount of surfactant(s) or emulsifier(s). The amount of the surfactant(s) or emulsifier(s) in the composition according to the present invention may be 0.1% by weight or less, preferably 0.01% by weight or less, and more preferably 0.001% by weight or less, relative to the total weight of the composition. It is in particular preferable that the composition according to the present invention include no surfactant or emulsifier.

[Composition]

Since the composition according to the present invention comprises at least one (b) oil, the composition according to the present invention can comprise at least one fatty phase.

On the other hand, since the composition according to the present invention comprises (c) water, the composition according to the present invention can comprise at least one aqueous phase.

The aqueous phase may comprise at least one $C_2$-$C_6$ monohydric alcohol. Two or more $C_2$-$C_6$ monohydric alcohols may be used in combination.

The $C_2$-$C_6$ monohydric alcohol suitable for the present invention may comprise from 2 to 5 carbon atoms, preferably from 2 to 4 carbon atoms, such as ethanol, isopropanol, propanol or butanol.

Ethanol and isopropanol, and preferably ethanol, are very particularly suitable for the present invention.

The amount of the $C_2$-$C_6$ monohydric alcohol in the composition according to the present invention may be 20% by weight or less, preferably 15% by weight or less, and more preferably 10% by weight or less, relative to the total weight of the composition. On the other hand, the amount of the $C_2$-$C_6$ monohydric alcohol in the composition according to the present invention is 5% by weight or more, preferably 6% by weight or more, and more preferably 7% by weight or more, relative to the total weight of the composition. For example, the amount of the $C_2$-$C_6$ monohydric alcohol may be from 5% to 20% by weight, preferably from 6% to 15% by weight, and more preferably from 7% to 10% by weight, in relation to the total weight of the composition.

The aqueous phase may comprise polyhydric alcohols containing 2 to 8 carbon atoms such as propylene glycol, ethylene glycol, 1,3-butylene glycol, dipropylene glycol, diethylene glycol, pentyleneglycol, hexyleneglycol, glycerin, and mixtures thereof.

The amount of the polyhydric alcohol(s) such as glycols, if present, in the aqueous phase according to the present invention may range from 0.1 to 15% by weight, preferably from 0.5 to 12% by weight, and more preferably from 1 to 8% by weight, relative to the total weight of the composition.

The composition according to the present invention can be in the form of an emulsion, an O/W emulsion or a W/O emulsion. It is preferable that the composition according to the present invention be in the form of an O/W emulsion, because it can provide a fresh sensation due to the (c) water which forms the outer phase thereof.

It is more preferable that the amount of the surfactant(s) or emulsifier(s) in the emulsion, in particular an O/W emulsion, be 0.1% by weight or less, preferably 0.01% by weight or less, and more preferably 0.001% by weight or less, relative to the total weight of the composition, because the surfactant(s) may negatively affect water-resistance. It is in particular preferable that the emulsion, in particular an O/W emulsion include no surfactant or emulsifier.

The composition according to the present invention may be intended to be used as a cosmetic composition. Thus, the cosmetic composition according to the present invention may be intended for application onto a keratin substance. Keratin substance here means a material containing keratin as a main constituent element, and examples thereof include the skin, scalp, nails, lips, hair, and the like. Thus, it is preferable that the cosmetic composition according to the present invention be used for a cosmetic process for the keratin substance, in particular skin.

Thus, the cosmetic composition according to the present invention may be a skin cosmetic composition, preferably a skin care composition or a skin makeup composition, in particular a composition for protecting skin from UV and/or pollutants in the air.

The composition according to the present invention can be prepared by mixing the above essential and optional ingredients in accordance with any of the processes which are well known to those skilled in the art.

The composition according to the present invention can be prepared by simple or easy mixing with a conventional mixing means such as a stirrer. Thus, strong shearing by, for example, a homogenizer is not necessary. Also, heating is not necessary.

[Film]

The composition according to the present invention can be used for easily preparing a film. The (a) particles can aggregate and integrate into a continuous film.

Thus, the present invention also relates to a process for preparing a film, preferably a cosmetic film, with a thickness of, preferably more than 0.1 μm, more preferably 1.5 μm or more, and even more preferably 2 μm or more, comprising:

applying onto a substrate, preferably a keratin substrate, more preferably skin, the composition according to the present invention; and drying the composition.

The upper limit of the thickness of the film according to the present invention is not limited.

Thus, for example, the thickness of the film according to the present invention may be 1 mm or less, preferably 500 μm or less, more preferably 300 μm or less, and even more preferably 100 μm or less.

Since the process for preparing a film according to the present invention includes the steps of applying the composition according to the present invention onto a substrate, preferably a keratin substrate, and more preferably skin, and of drying the composition, the process according to the present invention does not need any spin coating or spraying, and therefore, it is possible to easily prepare even a relatively thick film. Thus, the process for preparing a film according to present invention can prepare a relatively thick film without any special equipment such as spin coaters and spraying machines.

Even if the film according to the present invention is relatively thick, it is still thin and may be transparent, and therefore, may not be easy to perceive. Thus, the film according to the present invention can be used preferably as a cosmetic film.

If the substrate is not a keratin substrate such as skin, the composition according to the present invention may be applied onto a substrate made from any material other than keratin. The materials of the non-keratinous substrate are not limited. Two or more materials may be used in combination. Thus, a single type of material or a combination of different types of materials may be used. In any event, it is preferable that the substrate be flexible or elastic.

If the substrate is not a keratin substrate, it is preferable that the substrate be water-soluble, because it is possible to leave the film according to the present invention by washing the substrate with water. As examples of the water-soluble materials, mention may be made of poly(meth) acrylic acids, polyethyleneglycols, polyacrylamides, polyvinylalcohol (PVA), starch, celluloseacetates, and the like. PVA is preferable.

If the non-keratinous substrate is in the form of a sheet, it may have a thickness of more than that of the film according to the present invention, in order to ease the handling of the film attached to the substrate sheet. The thickness of the non-keratinous substrate sheet is not limited, but may be from 1 μm to 5 mm, preferably from 10 μm to 1 mm, and more preferably from 50 to 500 μm.

It is more preferable that the film according to the present invention be releasable from the non-keratinous substrate. The mode of release is not limited. Therefore, the film according to the present invention may be peeled from the non-keratinous substrate, or released by the dissolution of the substrate sheet into a solvent such as water.

The present invention also relates to:

(1) A film, preferably a cosmetic film, with a thickness of, preferably more than 0.1 µm, more preferably 1.5 µm or more, and even more preferably 2 µm or more, prepared by a process comprising:

applying onto a substrate, preferably a keratin substrate, and more preferably skin, the composition according to the present invention; and drying the composition, and (2) A film, preferably a cosmetic film, with a thickness of, preferably more than 0.1 µm, more preferably 1.5 µm or more, and even more preferably 2 µm or more, comprising:

at least one cationic polymer and at least one anionic polymer, at least one cationic polymer and at least one amphoteric polymer, at least one anionic polymer and at least one amphoteric polymer, or at least one amphoteric polymer;

at least one non-polymeric acid having two or more pKa values or salt(s) thereof or at least one non-polymeric base having two or more pKb values or salt(s) thereof, and at least one oil.

The above explanations regarding the cationic and anionic polymers as well as the above oil can apply to those in the above film (1) and (2).

The film thus obtained above can be self-standing. The term "self-standing" here means that the film can be in the form of a sheet and can be handled as an independent sheet without the assistance of a substrate or support. Thus, the term "self-standing" may have the same meaning as "self-supporting".

It is preferable that the film according to the present invention be hydrophobic.

The term "hydrophobic" in the present specification means that the solubility of the polymer in water (preferably with a volume of 1 liter) at from 20 to 40° C., preferably from 25 to 40° C., and more preferably from 30 to 40° C. is less than 10% by weight, preferably less than 5% by weight, more preferably less than 1% by weight, and even more preferably less than 0.1% by weight, relative to the total weight of the polymer. It is most preferable that the polymer is not soluble in water.

If the film according to the present invention is hydrophobic, the film can have water-resistant properties, and therefore, it can remain on a keratin substrate such as skin even if the surface of the keratin substrate is wet due to, for example sweat and rain. Thus, when the film according to the present invention provides any cosmetic effect, the cosmetic effect can last a long time.

On the other hand, the film according to the present invention can be easily removed from a keratin substrate such as skin under alkaline conditions such as a pH of from 8 to 12, preferably from 9 to 11. Therefore, the film according to the present invention is difficult to remove with water, while it can be easily removed with a soap which can provide such alkaline conditions.

The film according to the present invention may comprise at least one biocompatible and/or biodegradable polymer layer. Two or more biocompatible and/or biodegradable polymers may be used in combination. Thus, a single type of biocompatible and/or biodegradable polymer or a combination of different types of biocompatible and/or biodegradable polymers may be used.

The term "biocompatible" polymer in the present specification means that the polymer does not have excess interaction between the polymer and cells in the living body including the skin, and the polymer is not recognized by the living body as a foreign material.

The term "biodegradable" polymer in the present specification means that the polymer can be degraded or decomposed in a living body due to, for example, the metabolism of the living body itself or the metabolism of the microorganisms which may be present in the living body. Also, the biodegradable polymer can be degraded by hydrolysis.

If the film according to the present invention includes a biocompatible and/or biodegradable polymer, it is less irritable or not irritable to the skin, and does not cause any rash. In addition, due to the use of a biocompatible and/or biodegradable polymer, the cosmetic sheet according to the present invention can adhere well to the skin.

The film according to the present invention can be used for cosmetic treatments of keratin substances, preferably skin, in particular the face. The film according to the present invention can be in any shape or form. For example, it can be used as a full-face mask sheet, or a patch for a part of the face such as the cheek, nose, and around the eyes.

If the film according to the present invention includes at least one hydrophilic or water-soluble UV filter, it can provide UV shielding effects derived from the hydrophilic or water-soluble UV filter. Normally, a hydrophilic or water-soluble UV filter can be removed from the surface of a keratinous substrate such as skin by water such as sweat and rain. However, since the hydrophilic or water-soluble UV filter is included in the film according to the present invention, it is difficult for the hydrophilic or water-soluble UV filter to be removed by water, thereby resulting in long-lasting UV shielding effects.

[Cosmetic Process and Use]

The present invention also relates to:

a cosmetic process for a keratin substrate such as skin, comprising: applying to the keratin substrate the composition the present invention; and drying the composition to form a cosmetic film on the keratin substrate; and a use of the composition according to the present invention for the preparation of a cosmetic film on a keratin substrate such as skin.

The cosmetic process here means a non-therapeutic cosmetic method for caring for and/or making up the surface of a keratin substrate such as skin.

In both the above process and use, the above cosmetic film is resistant to water with a pH of 7 or less, and is removable with water with a pH of more than 7, preferably 8 or more, and more preferably 9 or more.

In other words, the above cosmetic film can be water-resistant under neutral or acidic conditions such as a pH of 7 or less, preferably in a range of 6 or more and 7 or less, and more preferably in a range of 5 or more and 7 or less, while the above cosmetic film can be removed under alkaline conditions such as a pH of more than 7, preferably 8 or more, and more preferably 9 or more. The upper limit of the pH is preferably 13, more preferably 12, and even more preferably 11.

Accordingly, the above cosmetic film can be water-resistant, and therefore, it can remain on a keratin substrate such as skin even if the surface of the keratin substrate is wet due to, for example sweat and rain. On the other hand, the above cosmetic film can be easily removed from a keratin substrate such as skin under alkaline conditions. Therefore, the film according to the present invention is difficult to remove with water, while it can be easily removed with a soap which can provide alkaline conditions.

If the above cosmetic film includes a UV filter which may be present in the composition according to the present invention, the above cosmetic film can protect a keratin substrate such as skin from UV rays, thereby limiting the darkening of the skin, improving the colour and uniformity of the complexion, and/or treating aging of the skin.

Furthermore, the above cosmetic film may have cosmetic effects such as absorbing or adsorbing malodor, changing the appearance of a keratin substrate such as skin, changing the feel to the touch of the keratin substrate, and/or protecting the keratin substrate from, for example, dirt or pollutant, due to the properties of the polyion complex particles in the cosmetic film, even if the cosmetic film does not include any cosmetic active ingredient.

In addition, the above cosmetic film may immediately change or modify the appearance of the skin by changing light reflection on the skin and the like, even if the cosmetic film does not include any cosmetic active ingredient. Therefore, it may be possible for the above cosmetic film to conceal skin defects such as pores or wrinkles. Further, the above cosmetic film may immediately change or modify the feel to the touch of the skin by changing the surface roughness on the skin and the like. Furthermore, the above cosmetic film may immediately protect the skin by covering the surface of the skin and shielding the skin, as a barrier, from environmental stresses such as pollutants, contaminants and the like.

The above cosmetic effects can be adjusted or controlled by changing the chemical composition, the thickness and/or the surface roughness of the above cosmetic film.

If the above cosmetic film includes at least one additional cosmetic active ingredient other than the (b) oil, the cosmetic film can have cosmetic effects provided by the additional cosmetic active ingredient(s). For example, if the cosmetic film includes at least one cosmetic active ingredient selected from anti-aging agents, anti-sebum agents, deodorant agents, anti-perspirant agents, whitening agents and a mixture thereof, the cosmetic film can treat the aging of the skin, absorbing sebum on the skin, controlling odors on the skin, controlling perspiration on the skin, and/or whitening of the skin.

It is also possible to apply a makeup cosmetic composition onto the cosmetic sheet according to the present invention after being applied onto the skin.

EXAMPLES

The present invention will be described in a more detailed manner by way of examples. However, they should not be construed as limiting the scope of the present invention.

[Preparation of Polyion Complex Particle 1]

1.50 g of a 10 wt % aqueous solution of carboxymethylcellulose (CMC) as a polyanion, 16.76 g of a 25 wt % aqueous solution of polylysine (PLYS) as a polycation, 0.58 g of a 40 wt % aqueous solution of sodium styrene/maleic acid copolymer (SMA) as a polyanion, 0.30 g of phenylalanine, 0.50 g of phenoxyethanol, and 50.06 g of water were mixed by using a stirrer. While stirring, 30.30 g of an aqueous solution containing 33 wt % of terephthalylidene dicamphor sulfonic acid (Mexoryl SX) was added to the above mixture. With the decrease of the pH of the mixture thus obtained, polyion complex gel particles (PGP) were formed. Thus, a stable PGP dispersion was successfully prepared. The final pH of the PGP dispersion was about 4-4.5. The number average particle size of the obtained particle was 800 nm.

The materials used to prepare the PGP dispersion according to Example 1 are shown in Table 1. The numerical values for the amounts of the ingredients shown in Table 1 are all based on g.

TABLE 1

| | amount |
|---|---|
| Carboxymethylcellulose (CMC) (MW 100,000) | 1.50 |
| Poly-ε-lysine (PLYS) (MW 5000) | 16.76 |
| Phenylalanine | 0.30 |
| Sodium Styrene/Maleic Acid Copolymer (SMA) | 0.58 |
| Phenoxyethanol | 0.50 |
| Terephthalylidene Dicamphor Sulfonic Acid (MSX) | 30.30 |
| Water | qsp 100 |

Mexoryl SX:

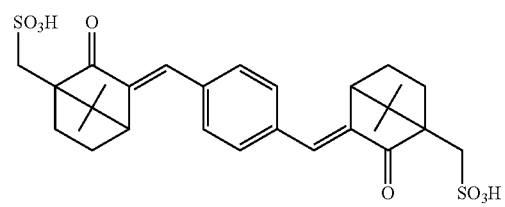 [SMILES: CC1(C)C2CCC1(CS(=O)(=O)O)C(=O)/C2=C/c1ccc(/C=C2/C(=O)C3(CS(=O)(=O)O)CCC2C3(C)C)cc1]

(Preparation of Emulsion)

An emulsion was prepared by using the PGP dispersion prepared as above. Each of the oily ingredients shown in Table 2 was added to the PGP dispersion, and mixed with a homogenizer at 2500 rpm for 20 minutes under the conditions that the amount of the PGP was 15% by weight relative to the total weight of the emulsion. The amount of each oily ingredient is also shown in Table 2. The numerical values for the amounts of the ingredients shown in Table 2 are all based on "% by weight".

TABLE 2

| | Ex. 1 | Ex. 2 | Ex. 3 | Ex. 4 | Ex. 5 | Ex. 6 | Ex. 7 | Ex. 8 |
|---|---|---|---|---|---|---|---|---|
| Mineral Oil | 10 | 20 | 29.01 | — | — | — | — | — |
| Ethylenediamine/Stearyl Dimer Dilinoleate Copolymer | — | — | 0.13 | — | — | — | — | — |
| Isononyl Isononanoate | — | — | — | 20 | 29.14 | — | — | — |
| Dimethicone | — | — | — | — | — | 20 | 29.14 | — |
| Caprylic/Capric Triglyceride | — | — | — | — | — | — | — | 29.14 |

TABLE 2-continued

|  | Ex. 1 | Ex. 2 | Ex. 3 | Ex. 4 | Ex. 5 | Ex. 6 | Ex. 7 | Ex. 8 |
|---|---|---|---|---|---|---|---|---|
| Stability | Very Stable | Very Stable | Stable | Very Stable | Very Stable | Stable | Stable | Very Stable |

(Evaluation 1)

The emulsions according to Examples 1 to 8 were stored for 1 month. The aspect of each emulsion was visually observed, and evaluated in accordance with the following criteria.

Very Stable: No phase separation was observed.

Stable: Slight phase separation was observed, but the aspect was almost homogeneous as a whole.

The results are shown in Table 2.

Table 2 shows that PGP can be used for preparing stable emulsions with a variety of oils. By using PGP, emulsions can be prepared without any surfactant. At least, up to about 30% by weight of oil can be used, but it may be preferable that the amount of oil be about 30% by weight or less.

Table 2 also shows that both polar and non-polar oils can be used to prepare emulsions. It may be preferable to use polar oils such as isononyl isononanoate and caprylic/capric triglyceride in terms of stability of emulsions. However, by combining with an oil gelling agent such as ethylenediamine/stearyl dimer dilinoleate copolymer, non-polar oil such as mineral oil can also be very stably emulsified.

(Evaluation 2)

An adequate small amount of pyranine and nile red were added to the emulsions according to Examples 1 to 8. Pyramine was used as a fluorescent marker for the aqueous phase of the emulsions. Nile red was used as a fluorescent marker for the oil phase of the emulsions.

The emulsions according to Examples 1 to 8 were observed with a fluorescent microscope. It was observed that oil was encapsulated with capsules made from the PGP. In other words, oil globules were coated with a thin film or layer made from the PGP. FIG. 1 shows oil globules encapsulated with capsules made from the PGP according to Example 1. Thus, the emulsions according to Examples 1 to 8 were a type of O/W emulsion.

It was found that the PGP is located on the interface between water and oil, as the PGP is amphiphilic and insoluble in water and oil, and that PGP encapsulation can be easily performed by a process of simply mixing a PGP dispersion and oil(s) without heating or strongly shearing.

[Preparation of Polyion Complex Particle 2]

Example 9

0.02 g of carboxymethylcellulose and 0.2 g of vegetable chitosan were dissolved into 60 g of water, and pH was adjusted to 2.5 by 4 wt % HCL aqueous solution. 1.5 g of an aqueous solution (10 wt %) of arginine was added to this mixture until pH reached 6.4. During the pH increase of the mixture, cationic polyion complex particles (cationic PGP), which were composed of carboxymethylcellulose (polyanion), chitosan (polycation) and arginine (cationic crosslinker), were successfully prepared.

The diameter of the cationic PGP was about 15 nm, and the ζ potential of the cationic PGP was 30 mV.

The cationic PGP dispersion according to Example 9 was stable for 2 weeks at room temperature. Thus, no precipitates were visually observed for 2 weeks.

Example 10

0.05 g of carboxymethylcellulose and 0.2 g of vegetable chitosan were dissolved into 60 g of water, and pH was adjusted to 1.8 by 4 wt % HCl aqueous solution. 3 g of an aqueous solution (10 wt %) of arginine was added to this mixture until pH reached 4.9. During the pH increase of the mixture, particles of cationic PGP, which were composed of carboxymethylcellulose (polyanion), chitosan (polycation) and arginine (cationic crosslinker), were successfully prepared.

The diameter of the cationic PGP was about 370 nm, and the ζ potential of the cationic PGP was 6 mV.

The cationic PGP dispersion according to Example 1 was stable for 2 weeks at room temperature. Thus, no precipitates were visually observed for 2 weeks.

[Preparation of Crosslinked Polyampholyte Particle 1]

As a polyanion, a 10 wt % aqueous solution of carboxymethylcellulose (CMC) was used. As a polycation, a 25 wt % aqueous solution of polylysine (PLYS) was used. As a polyampholyte, a 20.54 wt % aqueous solution of polyquaternium-53 was used.

For Examples 11-16, in accordance with the composition shown in Table 3 shown below, the ingredients shown in Table 3 except for terephthalylidene dicamphor sulfonic acid (Mexoryl SX: MSX) were added into a beaker, heated at 70° C., and mixed with a stirrer, such that the amount of each of the ingredients was as shown in Table 3. Then, an aqueous solution containing 33 wt % of MSX was added to the above mixture such that the amount of MSX was as shown in Table 3. With the decrease of the pH of the mixture thus obtained, crosslinked polyampholyte particles (CARP) were formed. Thus, a stable CARP dispersion was successfully prepared. The number average particle size of the obtained particle was 1 μm. The numerical values shown in Table 3 are all based on "% by weight" of the active material in each ingredient.

TABLE 3

|  | Ex. 11 | Ex. 12 | Ex. 13 | Ex. 14 | Ex. 15 | Ex. 16 |
|---|---|---|---|---|---|---|
| Carboxymethylcellulose (CMC) (MW 100,000) | 1.00 | — | — | — | — | 1.00 |
| Poly-ε-lysine (PLYS) (MW 5000) | — | — | — | 3.77 | 3.77 | — |
| Polyquaternium-53 | 5.00 | 5.00 | 5.00 | 5.00 | 5.00 | 5.00 |
| Phenylalanine | 0.30 | — | — | — | — | — |
| Terephthalylidene Dicamphor Sulfonic Acid (MSX) | 2.90 | 0.99 | 1.30 | 6.60 | 7.90 | 2.90 |

TABLE 3-continued

|  | Ex. 11 | Ex. 12 | Ex. 13 | Ex. 14 | Ex. 15 | Ex. 16 |
|---|---|---|---|---|---|---|
| Water | qsp 100 | qsp 100 | qsp 100 | qsp 100 | qsp 100 | qsp 100 |
| CARP Formation | Good | Good | Good | Good | Good | Good |
| Emulsion Stability | Stable | Stable | Stable | Stable | Stable | Stable |
| Water Resistivity | Good | Good | Good | Good | Good | Good |

[Preparation of Crosslinked Polyampholyte Particle 2]

As a polyanion, a 10 wt % aqueous solution of carboxymethylcellulose (CMC) was used. As a polyampholyte, a 9.25 wt % aqueous solution of polyquaternium-39 was used.

For Examples 17-21, in accordance with the composition shown in Table 4 shown below, the ingredients shown in Table 4 except for terephthalylidene dicamphor sulfonic acid (Mexoryl SX: MSX) and/or phytic acid were added into a beaker, heated at 70° C., and mixed with a stirrer, such that the amount of each of the ingredients was as shown in Table 4. Then, an aqueous solution containing 33 wt % of MSX and/or phytic acid was added to the above mixture such that the amount of MSX and/or phytic acid was as shown in Table 4. With the decrease of the pH of the mixture thus obtained, crosslinked polyampholyte particles (CARP) were formed. Thus, a stable CARP dispersion was successfully prepared. The number average particle size of the obtained particle was 1 μm. The numerical values shown in Table 4 are all based on "% by weight" of the active material in each ingredient.

TABLE 4

|  | Ex. 17 | Ex. 18 | Ex. 19 | Ex. 20 | Ex. 21 |
|---|---|---|---|---|---|
| Carboxymethylcellulose (CMC) (MW 100,000) | 1.00 | — | — | 1.00 | — |
| Polyquaternium-39 | 5.00 | 1.35 | 1.35 | 2.50 | 3.38 |
| Phenylalanine | 0.30 | 0.27 | — | 0.30 | — |
| Sodium Styrene/Maleic Acid Copolymer (SMA) | 0.20 | — | — | — | — |
| Terephthalylidene Dicamphor Sulfonic Acid (MSX) | — | 0.46 | 0.46 | 0.99 | 0.46 |
| Phytic Acid | 2.50 | — | — | 5.00 | — |
| Water | qsp 100 | qsp 100 | qsp 100 | qsp 100 | qsp 100 |
| CARP Formation | Good | Good | Good | Good | Good |
| Emulsion Stability | Stable | Stable | Stable | Stable | Stable |
| Water Resistivity | Good | Good | Good | Good | Good |

(Evaluation 3)

The aspect of the compositions according to Examples 11-21 was observed with microscopy, and evaluated in accordance with the following criteria.

Good: Particles were formed.

Poor: Particles were not formed.

The results are shown in the "CARP Formation" line in Tables 3 and 4.

[Preparation of Emulsion]

An emulsion was prepared by using the CARP dispersion prepared as above. Each of the oily ingredients shown below was added to the CARP dispersion, and mixed with a homogenizer at 2500 rpm for 20 minutes under the conditions that the amount of the CARP was 15% by weight relative to the total weight of the emulsion. The amount of each oily ingredient is also shown below. The numerical values for the amounts of the ingredients shown below are all based on "% by weight".

| ETHYLHEXYL TRIAZONE | 1.46 |
|---|---|
| OCTOCRYLENE | 0.50 |
| BIS-ETHYLHEXYLOXYPHENOL METHOXYPHENYL TRIAZINE | 0.49 |
| BUTYL METHOXYDIBENZOYLMETHANE | 1.40 |
| C12-15 Alkyl Benzoate | 1.01 |
| ETHYLENEDIAMINE/STEARYL DIMER DILINOLEATE COPOLYMER | 0.07 |
| ISONONYL ISONONANOATE | 5.00 |

(Evaluation 4)

The emulsions prepared with the CARP dispersion according to Examples 11-21 were stored at room temperature for 1 month. The aspect of each of the emulsion was visually observed, and evaluated in accordance with the following criteria.

Stable: no phase separation was observed, or slight phase separation was observed but the aspect was almost homogeneous as a whole.

Unstable: complete phase separation was observed.

The results are shown in "Emulsion Stability" line in Tables 3 and 4.

(Evaluation 5)

50 mg of the emulsion prepared with the CARP dispersion according to each of Examples 11-21 was applied onto a surface of a polymethylmethacrylate (PMMA) plate (HELIOPLATE HD6) and dried at room temperature for 1 hour.

After drying, the PMMA plate was dipped into a calcium chloride solution (0.14 g/l) at room temperature for 15 minutes.

After dipping, the PMMA plate was pulled up, and dried for 1 hour. The surface of the PMMA plate was visually observed, and evaluated in accordance with the following criteria.

Good: A film was present on the PMMA plate.

Poor: A film was not present on the PMMA plate.

The results are shown in the "Water Resistivity" line in Tables 3 and 4. The thickness of the obtained film was 1 m.

[Preparation of Emulsion]

As a polyampholyte, a 20.54 wt % aqueous solution of polyquaternium-53 was used.

In accordance with the composition shown in Table 5 shown below, the above ingredient and water were added into a beaker, heated at 70° C., and mixed with a stirrer, such that the amount of each of the ingredients was as shown in Table 5. Then, an aqueous solution containing 33 wt % of terephthalylidene dicamphor sulfonic acid (Mexoryl SX) was added to the above mixture such that the amount of Mexory SX was as shown in Table 5. With the decrease of the pH of the mixture thus obtained, crosslinked polyampholyte particles (CARP) were formed. Thus, a stable CARP dispersion was successfully prepared. The numerical values shown in Table 5 are all based on "% by weight" of the active material in each ingredient.

Then, the oily ingredients shown in Table 5 (cf. shaded lines) were added to the CARP dispersion, and mixed with a homogenizer at 6000 rpm for 20 minutes to prepare an emulsion according to Example 22. The amount of each of the oily ingredients is also shown in Table 5. The numerical values for the amounts of the ingredients shown in Table 5 are all based on "% by weight" of the active material in each ingredient.

TABLE 5

|  | Ex. 22 |
| --- | --- |
| Polyquaternium-53 | 10.00 |
| Water | 73.31 |
| Terephthalylidene Dicamphor Sulfonic Acid (MSX) | 2.60 |
| ETHYLHEXYL TRIAZONE | 1.46 |
| OCTOCRYLENE | 0.50 |
| BIS-ETHYLHEXYLOXYPHENOL METHOXYPHENYL TRIAZINE | 0.49 |
| BUTYL METHOXYDIBENZOYLMETHANE | 1.40 |
| C12-15 Alkyl Benzoate | 1.01 |
| ETHYLENEDIAMINE/STEARYL DIMER DILINOLEATE COPOLYMER | 0.07 |
| ISONONYL ISONONANOATE | 5.00 |

(Evaluation 6)

An adequate small amount of pyranine and nile red were added to the emulsions according to Example 22. Pyramine was used as a fluorescent marker for the aqueous phase of the emulsion. Nile red was used as a fluorescent marker for the oil phase of the emulsion.

The emulsion according to Example 22 was observed with a fluorescent microscope. It was observed that oil was encapsulated with capsules made from the CARP. In other words, oil globules were coated with a thin film or layer made from the CARP. Thus, the emulsion according to Example 22 is a type of O/W emulsion.

It was found that the CARP is located on the interface between water and oil, as the CARP is amphiphilic and insoluble in water and oil, and that CARP encapsulation can be easily performed by a process of simply mixing a CARP dispersion and oil(s) without heating or strongly shearing.

The invention claimed is:

1. A composition, comprising:
   (a) at least one polyion complex particle, comprising
   at least one cationic polymer and at least one anionic polymer,
   at least one cationic polymer and at least one amphoteric polymer,
   at least one anionic polymer and at least one amphoteric polymer, or
   at least one amphoteric polymer,
   and
   at least one crosslinker, selected from the group consisting of:
   at least one non-polymeric acid having two or more pKa values or salt(s) thereof, and
   at least one non-polymeric base having two or more pKb values or salt(s) thereof;
   (b) at least one oil; and
   (c) water;
   wherein
   the crosslinker crosslinks the cationic polymer and the anionic polymer, the cationic polymer and the amphoteric polymer, the anionic polymer and the amphoteric polymer, or the amphoteric polymer; and
   wherein the (a) particle further comprises (d) at least one hydrophobic amino acid other than the non-polymeric acid or base.

2. The composition according to claim 1, wherein a plurality of the (a) particles are present at the interface between the (b) oil and the (c) water, or a plurality of the (a) particles form a capsule having a hollow, and the (b) oil is present in the hollow.

3. The composition according to claim 1, wherein the cationic polymer has at least one positively chargeable and/or positively charged moiety selected from the group consisting of a primary, secondary or tertiary amino group, a quaternary ammonium group, a guanidine group, a biguanide group, an imidazole group, an imino group, and a pyridyl group.

4. The composition according to claim 1, wherein the cationic polymer is selected from the group consisting of cyclopolymers of alkyldiallylamine and cyclopolymers of dialkyldiallylammonium, (co)polyamines, cationic (co)polyaminoacids, and salts thereof.

5. The composition according to claim 1, wherein the anionic polymer has at least one negatively chargeable and/or negatively charged moiety selected from the group consisting of a sulfuric group, a sulfate group, a sulfonic group, a sulfonate group, a phosphoric group, a phosphate group, a phosphonic group, a phosphonate group, a carboxylic group, and a carboxylate group.

6. The composition according to claim 1, wherein the anionic polymer is selected from the group consisting of polysaccharides, anionic (co)polyaminoacids, (co)poly (meth)acrylic acids, (co)polyamic acids, (co)polystyrene sulfonate, (co)poly(vinyl sulfates), dextran sulfate, chondroitin sulfate, (co)polymaleic acids, polyfumaric acids, maleic acid (co)polymers, and salts thereof.

7. The composition according to claim 1, wherein the amphoteric polymer has
   at least one positively chargeable and/or positively charged moiety selected from the group consisting of a primary, secondary or tertiary amino group, a quaternary ammonium group, a guanidine group, a biguanide group, an imidazole group, an imino group, and a pyridyl group,
   and
   at least one negatively chargeable and/or negatively charged moiety selected from the group consisting of a sulfuric group, a sulfate group, a sulfonic group, a sulfonate group, a phosphoric group, a phosphate group, a phosphonic group, a phosphonate group, a carboxylic group, and a carboxylate group.

8. The composition according to claim 1, wherein the amphoteric polymer is selected from the group consisting of polyquaternium-22, polyquaternium-39, polyquaternium-53, polyquaternium-64, polyquaternium-51, polyquaternium-61, and mixtures thereof.

9. The composition according to claim 1, wherein the amount of the polymer(s), in the composition is from 0.001 to 25% by weight, relative to the total weight of the composition.

10. The composition according to claim 1, wherein the amount of the non-polymeric acid having two or more pKa values or salt(s) thereof or non-polymeric base having two or more pKb values or salt(s) thereof in the composition is from 0.0001 to 30% by weight, relative to the total weight of the composition.

11. The composition according to claim 1, wherein the pH of the composition is from 3 to 9.

12. The composition according to claim 1, wherein the amount of the (a) particle in the composition is from 0.001 to 60% by weight, relative to the total weight of the composition.

13. The composition according to claim 1, wherein the (b) oil is selected from polar oils.

14. The composition according to claim 1, wherein the amount of the (b) oil(s) in the composition is from 0.01 to 50% by weight, relative to the total weight of the composition.

15. The composition according to claim 1, wherein the composition is in the form of an emulsion comprising 0.1% by weight or less of surfactant(s).

16. The composition according to claim 1, wherein the composition further comprises (e) at least one oil gelling agent.

17. A film, prepared by a process comprising:
applying onto a substrate, the composition according to claim 1; and
drying the composition.

18. A film, comprising:
at least one cationic polymer and at least one anionic polymer,
at least one cationic polymer and at least one amphoteric polymer,
at least one anionic polymer and at least one amphoteric polymer, or
at least one amphoteric polymer; and
at least one crosslinker selected from the group consisting of:
at least one non-polymeric acid having two or more pKa values or salt(s) thereof, and
at least one non-polymeric base having two or more pKb values or salt(s) thereof;
and
at least one oil;
wherein
the crosslinker crosslinks the cationic polymer and the anionic polymer, the cationic polymer and the amphoteric polymer, the anionic polymer and the amphoteric polymer, or the amphoteric polymer; and
wherein the (a) particle further comprises (d) at least one hydrophobic amino acid other than the non-polymeric acid or base.

19. A process for preparing a film, comprising:
applying onto a substrate, the composition according to claim 1; and
drying the composition.

20. A cosmetic process for caring for and/or making up the surface of a keratin substrate, comprising
applying to the keratin substrate the composition according to claim 1; and
drying the composition to form a cosmetic film on the keratin substrate.

21. A process for preparing a film, comprising: applying onto a substrate, the composition according to claim 1; and drying the composition, wherein the cosmetic film is resistant to water with a pH of 7 or less, and is removable with water with a pH of more than 7.

* * * * *